(12) United States Patent
Jang et al.

(10) Patent No.: US 6,391,585 B1
(45) Date of Patent: May 21, 2002

(54) PROCESS FOR PREPARING RECOMBINANT PROTEINS USING HIGHLY EFFICIENT EXPRESSION VECTOR FROM SACCHAROMYCES CEREVISIAE

(75) Inventors: Ki-Ryong Jang; Jae-Woong Moon; Cheon-Soon Bae; Doo-Suk Yang; Jee-Won Lee; Baik-Lin Seong, all of Yusong-ku (KR)

(73) Assignee: Hanil Synthetic Fiber Co., Ltd., Masan-si (KR)

(*) Notice: Subject to any disclaimer, the term of this patent is extended or adjusted under 35 U.S.C. 154(b) by 0 days.

(21) Appl. No.: 09/424,620

(22) PCT Filed: May 27, 1997

(86) PCT No.: PCT/KR97/00097

§ 371 Date: Nov. 24, 1999

§ 102(e) Date: Nov. 24, 1999

(87) PCT Pub. No.: WO98/54339

PCT Pub. Date: Dec. 3, 1998

(51) Int. Cl.[7] .......... C12N 15/12; C12N 15/18; C12N 15/19; C12N 15/63; C12N 1/19; C07H 21/04

(52) U.S. Cl. .......... 435/69.1; 435/69.4; 435/69.5; 435/320.1; 435/254.21; 536/23.1; 536/24.1

(58) Field of Search .............. 536/23.1, 24.1; 435/320.1, 254.21, 69.1, 69.4, 69.5

(56) References Cited

U.S. PATENT DOCUMENTS

| | | | | |
|---|---|---|---|---|
| 5,013,652 A | * | 5/1991 | Strausberg et al. | 435/69.2 |
| 5,563,046 A | * | 10/1996 | Mascarenhas et al. | 435/69.52 |
| 5,939,287 A | * | 8/1999 | Makarow | 435/69.7 |
| 6,107,057 A | * | 8/2000 | Crawford et al. | 435/69.1 |

FOREIGN PATENT DOCUMENTS

WO    WO-00920 A2 * 1/1991

* cited by examiner

Primary Examiner—David Guzo
Assistant Examiner—Katharine F Davis
(74) Attorney, Agent, or Firm—Bachman & LaPointe, P.C.

(57) ABSTRACT

This invention concerns a method of producing human granulocyte colony-stimulating factor (hGCSF) and human growth hormone (hGH) from least by using recombinant DNA technology. More specifically, this invention relates to a method of producing hGCSF or hGH by using yeast expression vector which contains: hybrid promoters comprising promoters of two different yeast-derived genes, yeast killer toxin leader peptide, and amino terminus of IL-1β. In addition, this invention relates to a method of producing hGCSF by using expression vector which contains promoter and secretion signal of HSP 150.

16 Claims, 13 Drawing Sheets killer toxin leade:
Met-Asn-Ile-Phe-Tyr-Ile-Phe-Leu-Phe-Leu-Leu-Ser-Phe-

IL-1ß

Val-Gln-Gly-Thr-Arg-Gly-Ser-Leu-Asn-Cys-Thr-Leu-Argsignal peptidase ↑

Asp-Ser-Gln-Gln-Lys-Ser-Leu-Val-Met-Ser-Gly-Pro-TyrhGH

Glu-Leu-Lys-Ala-Gly-Val-Ser-Leu-Asp-Lys-Arg-Phe-Pro-

KEX2    ↑

Thr-Ile-Pro-Leu-Ser-Arg-Leu-Phe-Asp-Asn-Ala-Met-Leu-

Arg-Ala-His-Arg-Leu-His-Gln-Leu-Ala-Phe-Asp-Thr-Tyr-

Gln-Glu-Phe-Glu-Glu-Ala-Tyr-Ile-Pro-Lys-Glu-Gln-Lys-

Tyr-Ser-Phe-Leu-Gln-Asn-Pro-Gln-Thr-Ser-Leu-Cys-Phe-

Ser-Glu-Ser-Ile-Pro-Thr-Pro-Ser-Asn-Arg-Glu-Glu-Thr-

Gln-Gln-Lys-Ser-Asn-Leu-Glu-Leu-Leu-Arg-Ile-Ser-Leu-

Leu-Leu-Ile-Gln-Ser-Trp-Leu-Glu-Pro-Val-Gln-Phe-Leu-

Arg-Ser-Val-Phe-Ala-Asn-Ser-Leu-Val-Tyr-Gly-Ala-Ser-

Asp-Ser-Asn-Val-Tyr-Asp-Leu-Leu-Lys-Asp-Leu-Glu-Glu-

Gly-Ile-Gln-Thr-Leu-Met-Gly-Arg-Leu-Glu-Asp-Gly-Ser-

Pro-Arg-Thr-Gly-Gln-Ile-Phe-Lys-Gln-Thr-Tyr-Ser-Lys-

Phe-Asp-Thr-Asn-Ser-His-Asn-Asp-Asp-Ala-Leu-Leu-Lys-

Asn-Tyr-Gly-Leu-Leu-Tyr-Cys-Phe-Arg-Lys-Asp-Met-Asp-

Lys-Val-Glu-Thr-Phe-Leu-Arg-Ile-Val-Gln-Cys-Arg-Ser-

Val-Glu-Gly-Ser-Cys-Gly-Phe

FIG. 5

1: size marker
2,3: pIL20GC
4: non-transformant

1: size marker
2: YEpHSPGC

BSA: Bovine serum albumin

BSA: Bovine serum albumin

PROCESS FOR PREPARING RECOMBINANT PROTEINS USING HIGHLY EFFICIENT EXPRESSION VECTOR FROM SACCHAROMYCES CEREVISIAE

BACKGROUND OF THE INVENTION

The present invention relates to a process for preparing recombinant proteins from yeast by using recombinant DNA technology. More particularly, the present invention relates to a process for preparing recombinant proteins by using yeast expression vectors which comprise hybrid promoter consisting of two kinds of yeast inducible promoters and secretory signal consisting of yeast killer toxin and the amino terminus of mature interleukin 1β(IL-1β).

In addition, the present invention relates to a process for preparing recombinant proteins such as hGCSF and hGH from yeast by using the yeast expression vector which comprises promoter and secretory signal of yeast heat shock protein 150.

In addition, the present invention relates to a process for preparing recombinant proteins by using the yeast expression vector with XbaI cleavage site inserted in order to facilitate the insertion of the recombinant protein genes.

By using the present expression vector, the recombinant proteins such as human granulocyte colony-stimulating factor(hGCSF) and human growth hormone(hGH) can be produced with high secretion efficiency. An experiment of bone marrow differentiation and proliferation has disclosed that the colony of neutrophilic granulocyte or monocytic macrophage is formed, and thereafter it has been known that colony stimulation factors exist in the living body [J. Cell. Comp. Physiol. 66: 319 (1965); Aust. J. Exp. Biol. Med. Sci. 44: 287 (1966)].

The factors called as colony stimulating factor (hereinafter it refers to "CSF")are classified by their characteristics in biological activity as follows:

(i) GM-CSF (granulocyte-macrophage CSF) proliferates and differentiates stem cell of granulocytic leucocyte and monocytic macrophage, and finally forms colonies, (ii) M-CSF (macrophage CSF) forms colony of monocytic macrophages, iii) multi-CSF (multi-lineage CSF) stimulates undifferentiated pluripotent stem cells and finally forms colony of pluripotent cells, (iv) G-CSF (granulocyte CSF) forms colony of granulocyte leucocytes [J. B. C. 252: 1998–2033 (1977), J. B. C. 252: 4045–4052 (1977), Biochem. J. 185: 341–343 (1980), J. B. C. 258: 9017–9021 (1983)].

GCSF, about 20 kDa glycoprotein, is derived from monocyte, monocytic macrophage, epithelial cell, fibroblast etc. And human GCSF (hereinafter it refers to "hGCSF") gene exists on 17th chromosome. It is known that GCSF stimulates production of neutrophilia colony in vitro and of colonies of blast cell, macrophage in cooperation with IL-3, and get some myeloid leukemic cell line matured. GCSF increases the number of neutrophil and monocyte in vitro.

The clinical applications of hGCSF are as follows:

First, hGCSF increases the number of neutrophil dosage-dependently in treating a neutropenic patients with advanced solid and hematologic malignances.

Second, hGCSF recovers patients rapidly from neutropenia by chemotherapy for malign lymphatic tumor, lung cancer, testis cancer, urethra epithelioma and acute leukemia etc.

Third, hGCSF increases the number of neutrophil upon bone marrow transplantation for acute nonlymphocytic leukemia and chronic bone marrow leukemia patient.

Fourth, hGCSF recovers patients rapidly from neutropenia due to bone marrow dysplasia syndrome.

Fifth, hGCSF recovers patients rapidly from neutropenia due to aplastic anemia.

Sixth, hGCSF is useful for hereditary and idiopathic neutropenia.

Seventh, hGCSF prevents or reduces the incidence of mucositis and febrile neutropenia due to anti-tumor chemical treatment (Drug Evaluations Annual 1993, American Medical Associations p2232–2333).

Human growth hormone (hereinafter it refers to "hGH") is nonglycosylated protein which is made up of 191 amino acids, and it is secreted from pituitary anterior lobe. The hGH containing 2 intramolecular disulfide bonds has 22,000 dalton of molecular weight. It is initially synthesized as a precursor and is secreted from the cell after processing. The hGH is produced in large quantities before adulthood, and is produced during a whole human life.

The hGH is necessary for normal growth and development, but several types of dwarfism are caused by the abnormal low-level production of hGH and the over production of hGH can be accompanied by acromegaly or gigantism.

The hGH shows various biological activities and reacts to various tissues, directly or indirectly. It has an effect on linear bone growth rate and lactation, and shows diabetogenic insulin-like activity. In addition, it promotes protein synthesis, and has an effect on metabolism of lipid and carbohydrate.

The followings are clinical applications of hGH:

It is known that abnormal growth can be recovered if the hGH is administrated at the childhood in the case of dwarfism caused by deficiency of hGH [Raben, M. S., J. Clin. Endocr. 18 901–904 (1958)]. It is known that hGH is also used for treatment of obesity, and effective on treatment of various ailments such as bone fracture, skin burn, bleeding ulcer etc [Proc. of NIAMDD Symp. Publ. No. 74-612 (ed. Raiti, S.) (Baltimore, Md., 1973)].

Base sequence of hGH DNA is known by cDNA cloning of this gene, and the expression of hGH DNA in E. coli has been reported [Martial et al., Science 205: 602–605 (1979)].

Many genetic engineering methods have been attempted for the overproduction of recombinant proteins.

First, a method of expressing protein in E. coli after cloning the target gene has been developed [Science 232: 61–64 (1986)]. But there are some disadvantages in the method using E. Coli as a host as described in the followings.

In a human body, protein is synthesized as precursor first and then is processed to mature form by proteolysis.

But when the protein is expressed in E. coli, the N-terminal methionine of the synthesized protein is not so effectively removed by the aminopeptidase as in the human body and hence the proteins with and without the methionine can coexist in the cytoplasm of E. coli. Then it is very difficult to separate the protein without methionine from the protein with methionine.

In many cases, protein is expressed in inactive, or insoluble form and then it should be converted to biologically active protein through a renaturation(refolding) process where the recovery yield of protein is sometimes significantly reduced.

And there is a problem of contamination by bacterial endotoxin in the purification process.

In addition, the post-translational modification of protein (e.g. glycosylation of hGCSF) is not possible in E. coli.

Secondly, the cloned target gene has been expressed in animal cell such as CHU-2 (human GCSF-producing tumor cell line) or Chinese hamster ovary cell.

But the method using animal cell as a host has such disadvantages that culture condition is complicated with expensive serum media and recovery yield is generally very low since small amount of recombinant protein is usually purified from large volume of culture media [EMBO J. 5: 871–876 (1980)], (KR 91-5624).

As a plausible solution to the above problems, the expression system using yeast as a host has been developed. The method that can obtain target polypeptides or proteins in large amounts from recombinant yeast has been reported by Loison and others [Bio/Technol. 4:433–437 (1986); Burrow, "Baker's yeast, p349–420, in The Yeast, vol. 3, Rose and Harrison, eds. Academic Oress, London (1970)]. The expression system of recombinant yeast has significant advantages compared to the other expression systems employing animal cell or E. coli as a host.

The present inventors have studied a process of preparing hGCSF by using yeast. U. S. FDA noticed that yeast is not pathogenic to human body and most of regulation principles of gene expression in yeast are disclosed [Strathern et al., The Molecular Biology of the Yeast Saccharomyces, Metabolism and Gene Expression, Cold Spring Harbor Laboratory, New York (1982)].

Using yeast as host cell has advantages that it is generally regarded as safe organism to human body, and that it is possible to produce the large amount of hGCSF from high cell density cultures, and the purification process is simplified because soluble protein is secreted from the cells, being directed by the signal peptide.

Recently methods of expressing heterologous proteins such as B-type hepatitis virus, inteferon, calf chymosin, epidemal growth factor in yeast have been reported [Valensuela et al., Nature 298: 347–350 (1982); Hitzeman et al., NAR 11: 2745–2763 (1983); McAleer et al., Nature 307: 178–180(1984); Tuite et al., EMBO, J. 1: 603–608 (1982); Mellor et al., Gene 24: 1–14 (1983); Urdea et al., PNAS 80: 7461–7465 (1983)].

But the expression level of heterologous proteins in recombinant yeast is generally low very in comparison with that of homologous proteins in yeast, and therefore, the extensive efforts for developing the efficient expression vectors have been make to increase the expression level of heterologous in proteins in yeast [Chen et al., NAR 12: 8951–8970 (1984)].

For example, EP 84303833 discloses a process to prepare galactokinase-bovine prochymosin fusion protein from yeast by using a cloning vector with foreign target gene and yeast GALL promoter. Also in case that GAL4 gene of yeast is inserted to the expression vector containing exogenous gene and GAL1 promotor, the expression of GAL4 protein is increased via the transcription-level control by galactose, and hence the synthesis of the foreign protein can be increased [Laughon et al., PNAS 79: 6827–6831 (1982)]

EP 84302723 discloses a method of expressing human interferon, human serum albumin, bovine interferon α-1, α-2, tissue plasminogen activator, rennin, and human insulin-like growth factor in yeast by using the signal sequence and promoter of mating factor α.

SUMMARY OF THE INVENTION

The object of the present invention is to provide a process for preparing recombinant proteins from yeast by using recombinant DNA technology. Precisely, the present invention provides to a process for preparing recombinant proteins by using yeast expression vectors which consist of hybrid promoter consisting of two kinds of yeast inducible promoters and secretory signal consisting of yeast killer toxin and amino terminal of mature interleukin 1β(IL-1β).

The object of the present invention is to provide a process for preparing hGCSF from yeast by using expression vector made up of promoter and secretory signal of yeast heat shock protein 150.

The object of the present invention is to provide a process for preparing recombinant proteins by using yeast expression vector with XbaI cleavage site inserted in order to facilitate to insert the recombinant protein genes.

BRIEF DESCRIPTION OF DRAWING

In the accompanying figures;

FIG. 5 shows an amino acid sequence (SEQ ID NO: 25) consisting of killer toxin leader, N-terminal 24 residues, of IL-1β, and hGCSF, and cleavage sites digested by signal peptidase and by KEX2 peptidase.

DETAILED DESCRIPTION OF THE INVENTION

Figure 1:
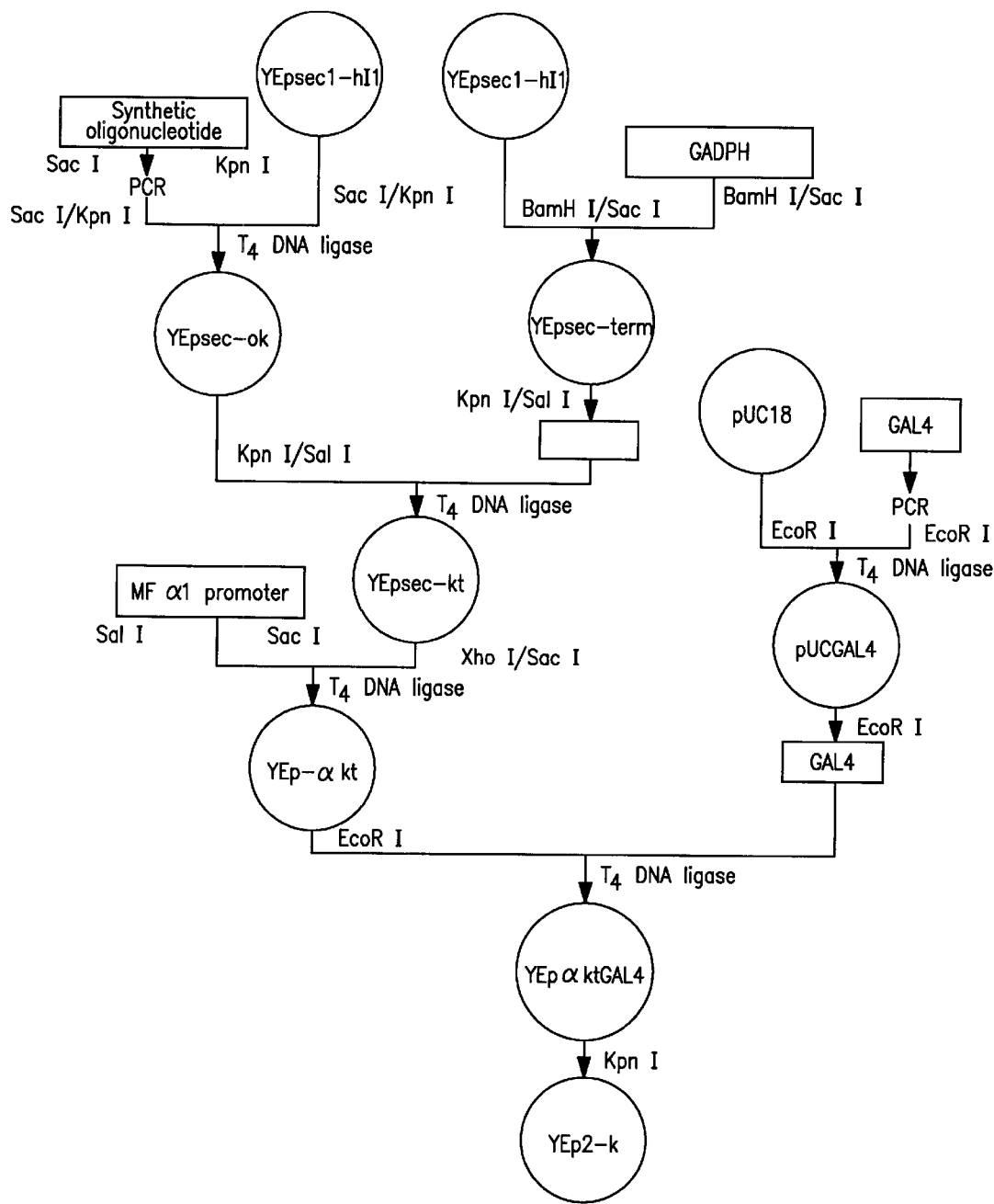
FIG. 1 shows a process for preparing YEp2-k
Figure 2:
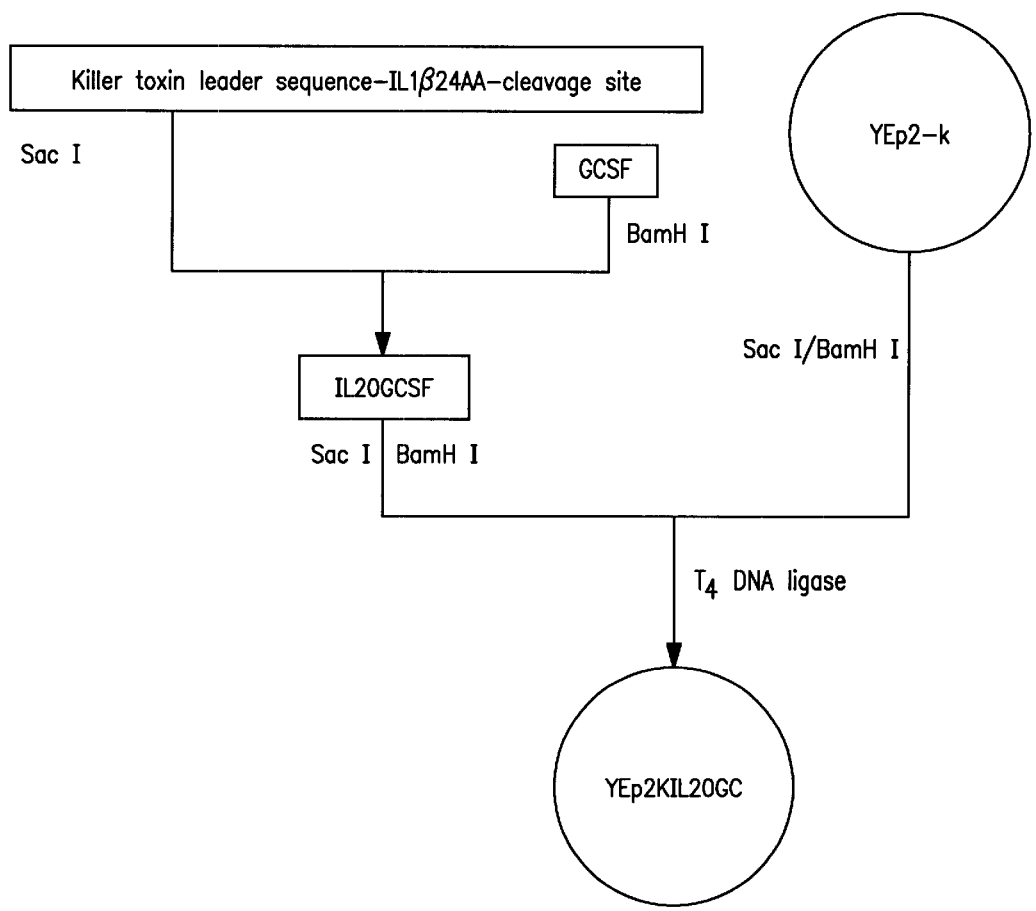
FIG. 2 shows a process for preparing YEp2KIL20GC
Figure 3:
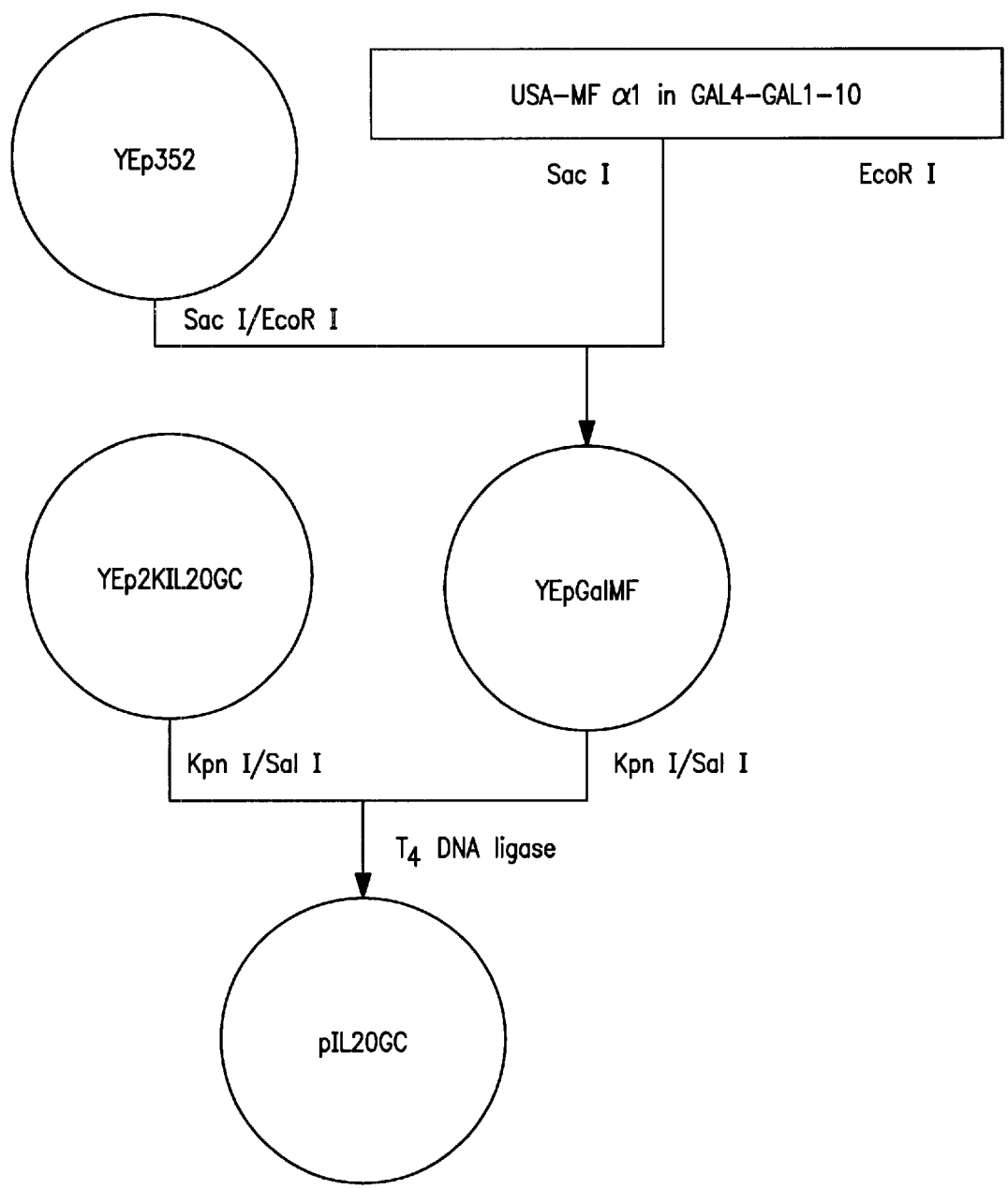
FIG. 3 shows a process for preparing pIL20GC
Figure 4:
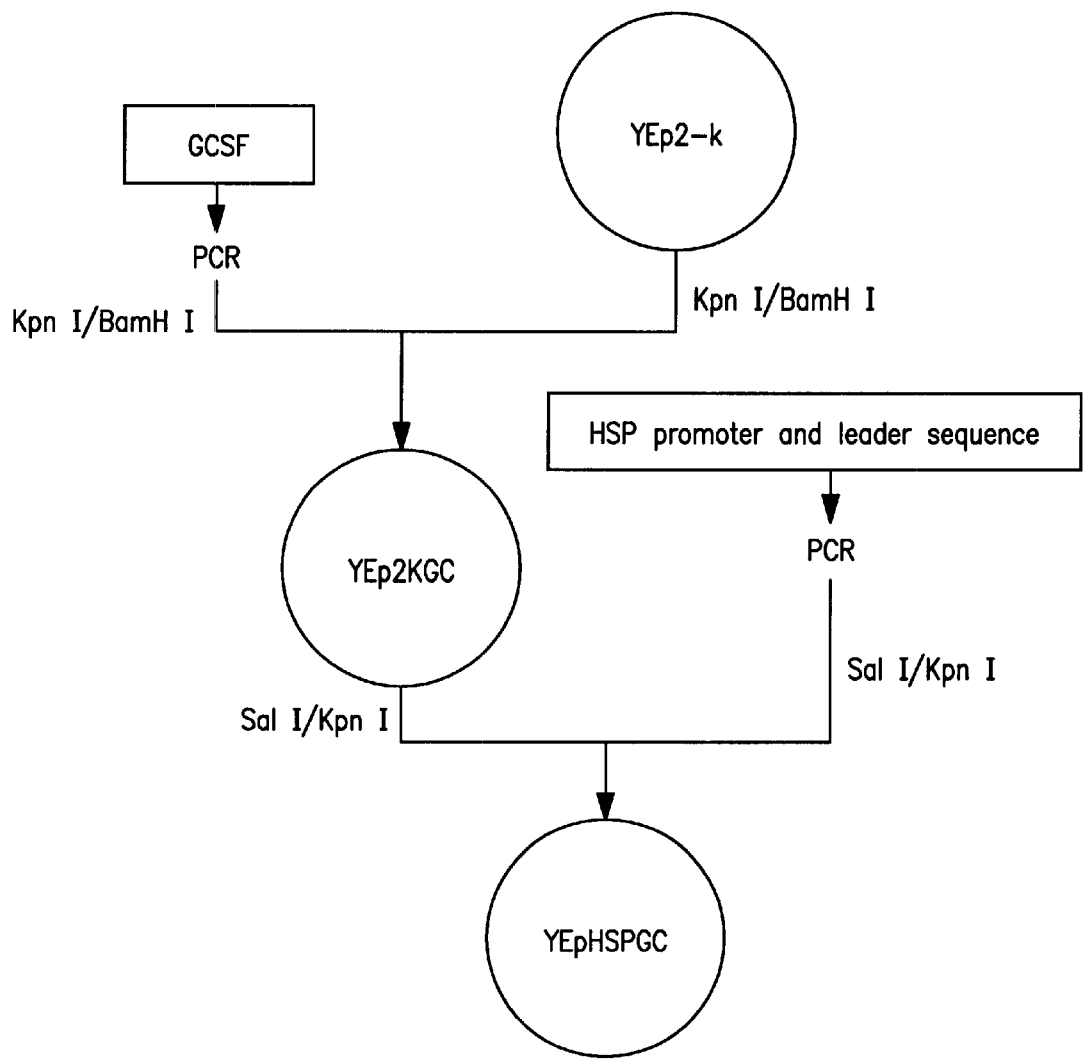
FIG. 4 shows a process for preparing YEpHSPGC
Figure 6:
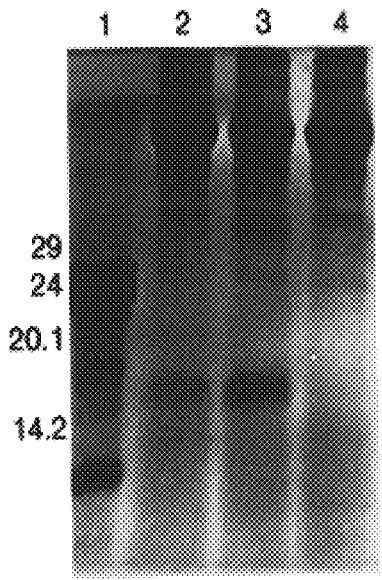
FIG. 6 shows a SDS-PAGE analysis of hGCSF expressed in yeast
Figure 7:
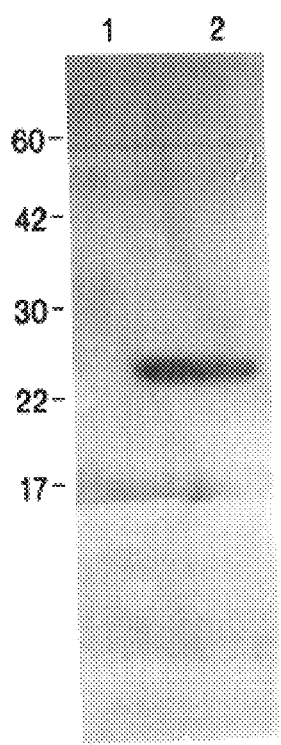
FIG. 7 shows a result of western blotting of hGCSF which is expressed in yeast by using yeast expression vector, YEpHSPGC
Figure 8:
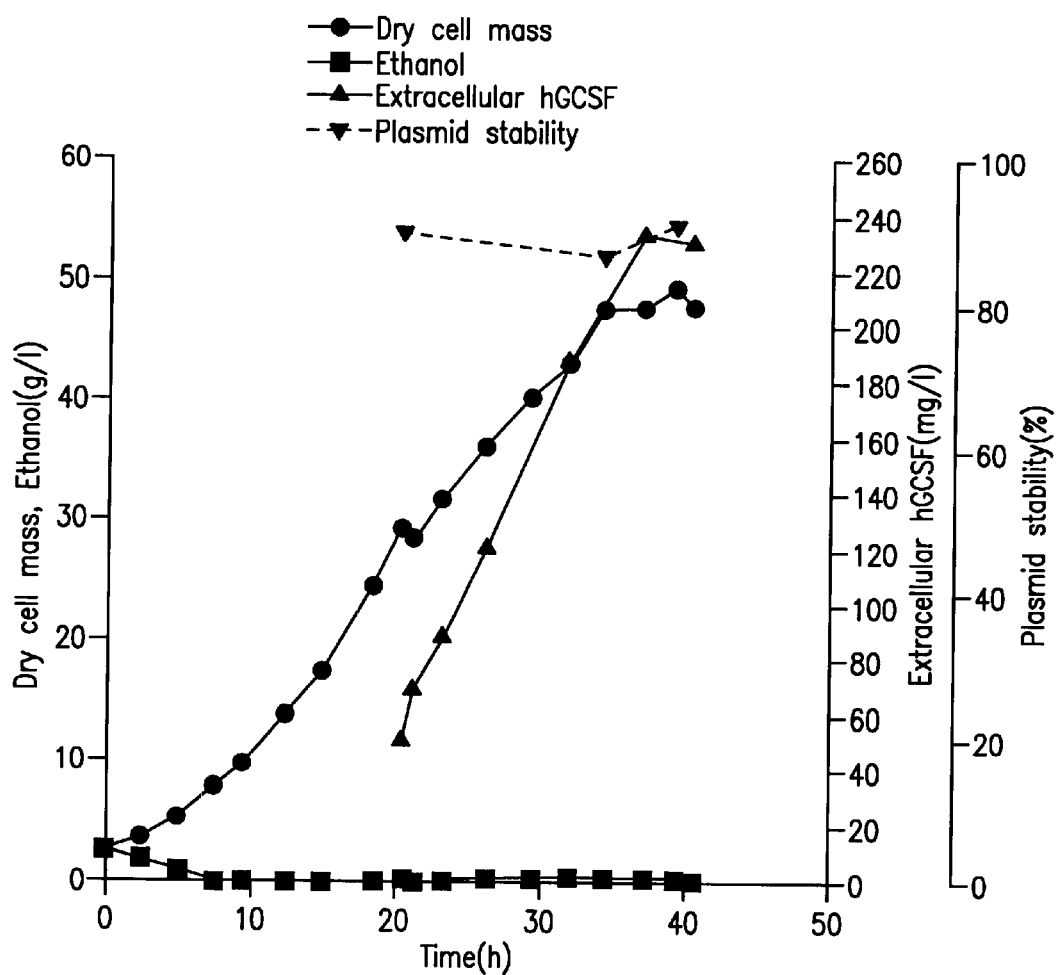
FIG. 8 is a gragh showing the time-course variation in cell, ethanol, and hGCSF concertrations and plasmid stability.
Figure 9:
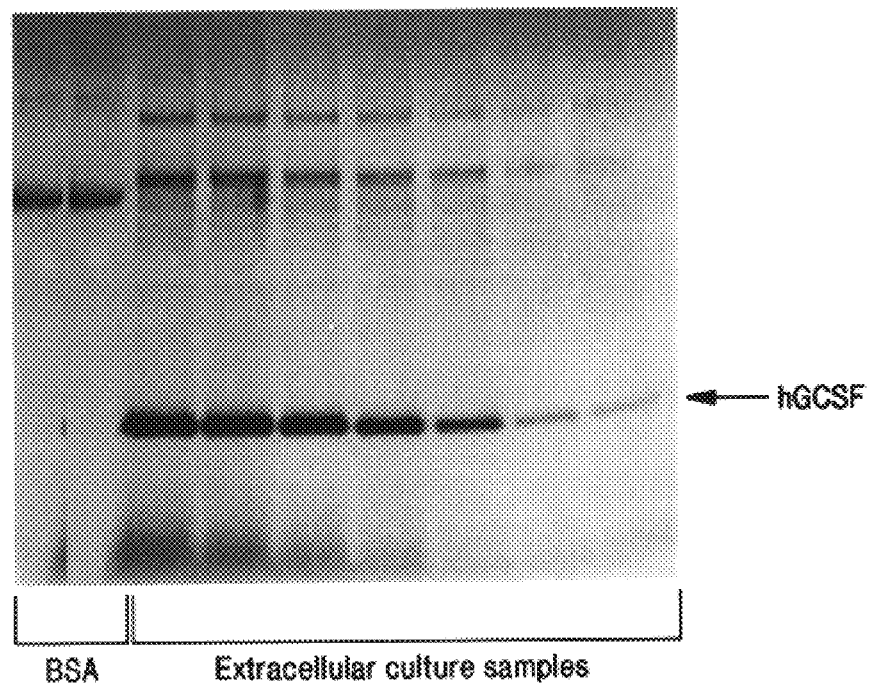
FIG. 9 shows a SDS-PAGE analysis of hGCSF expressed in yeast
Figure 11:
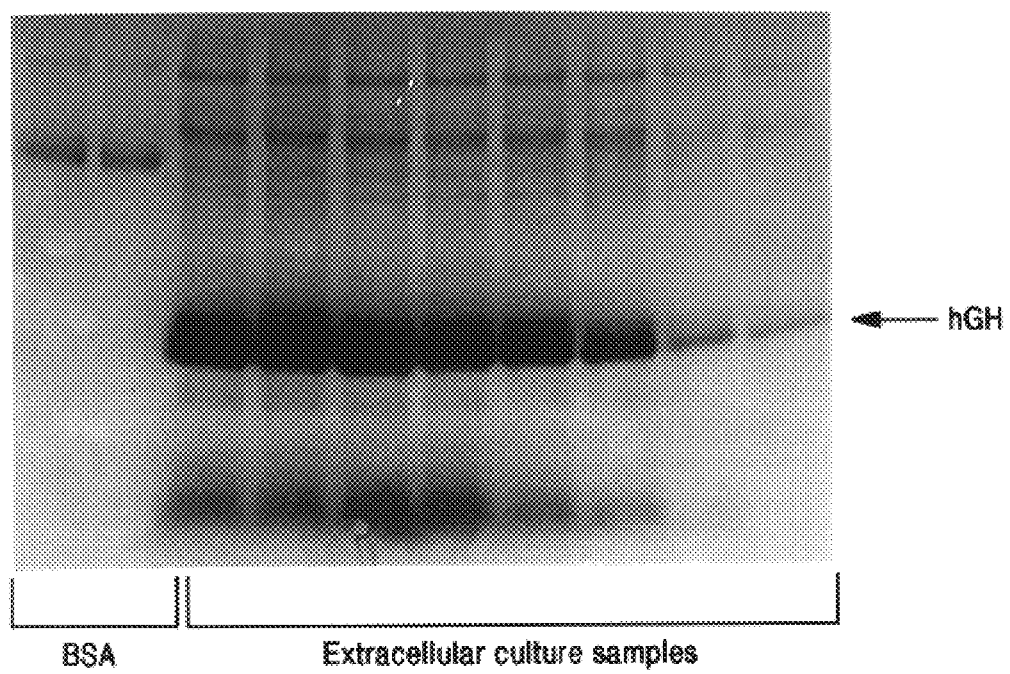
FIG. 11 shows a SDS-PAGE analysis of hGH expressed in yeast
Figure 10:
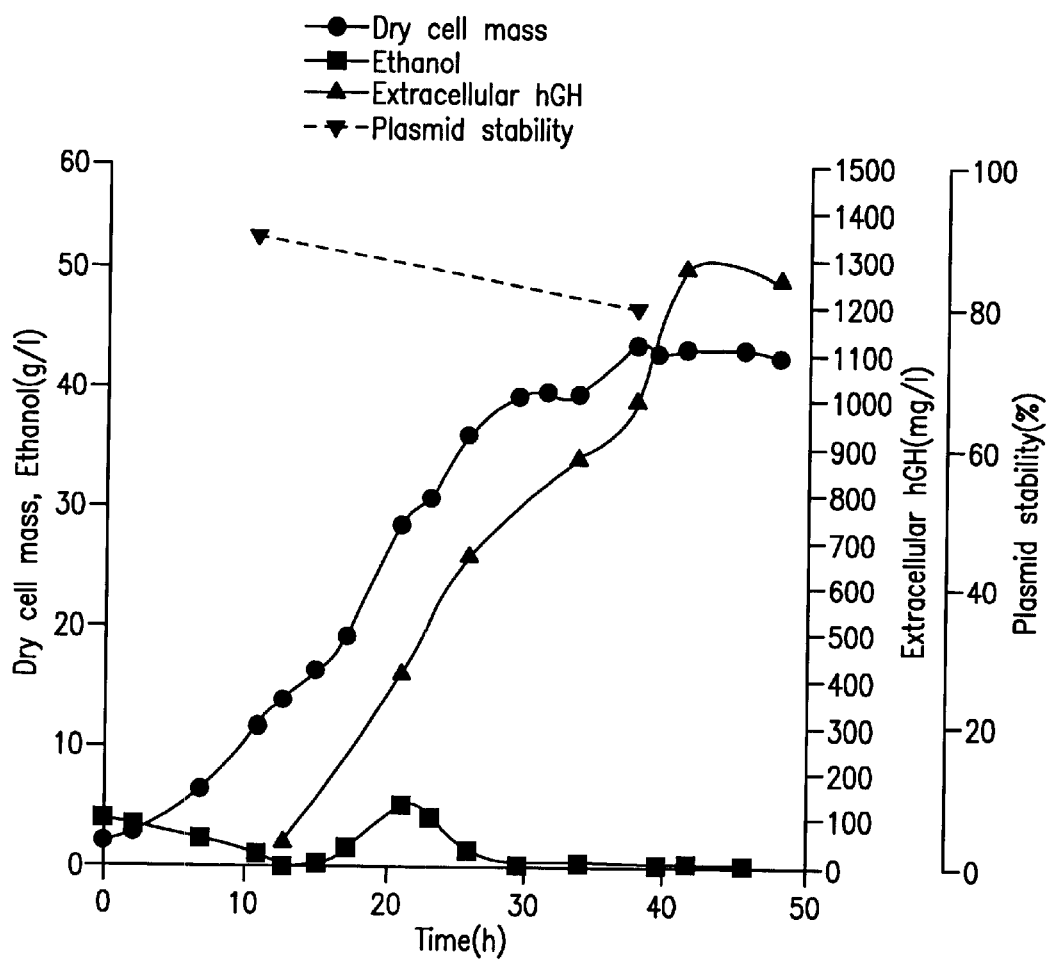
FIG. 10 is a gragh showing the time-course variation in cell, ethanol, and hGH concentrations and plasmid stability.
Figure 12:
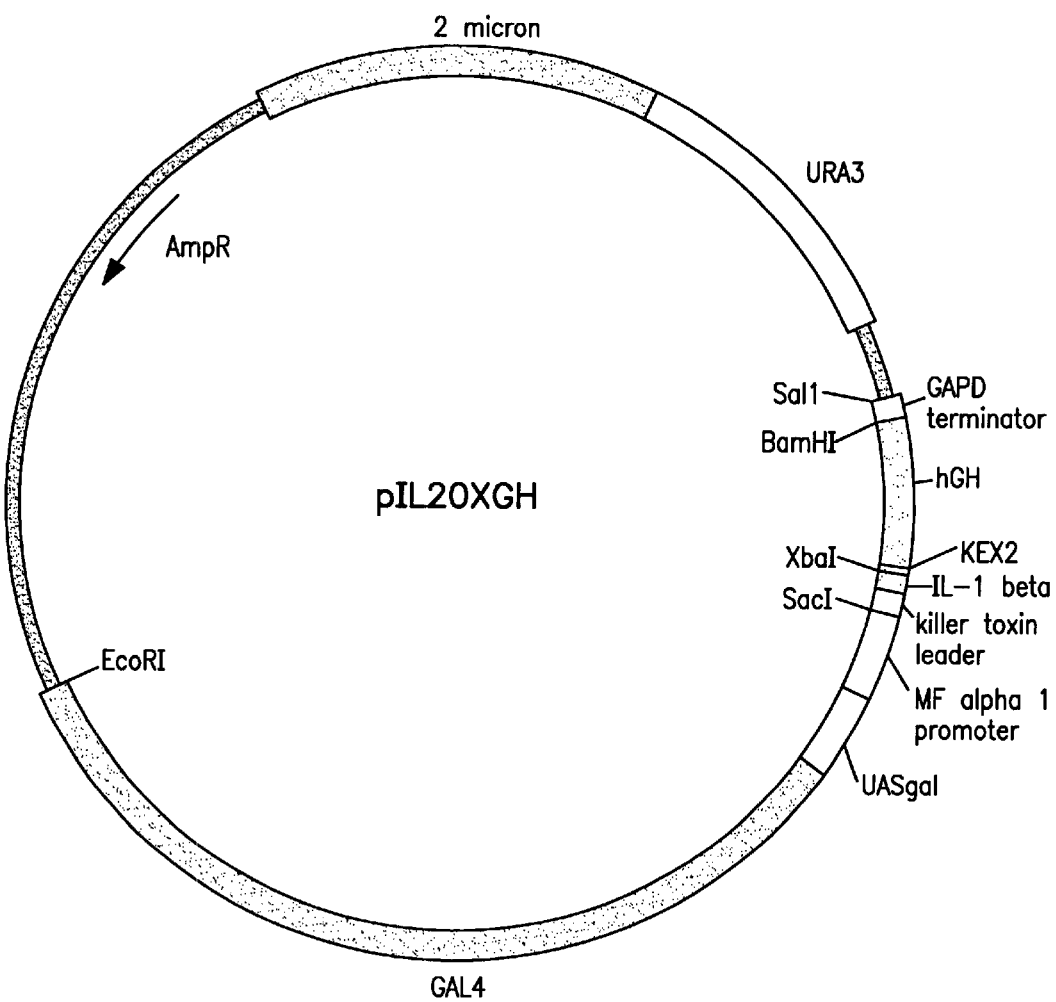
FIG. 12 is a map of pIL20XGH
Figure 13:
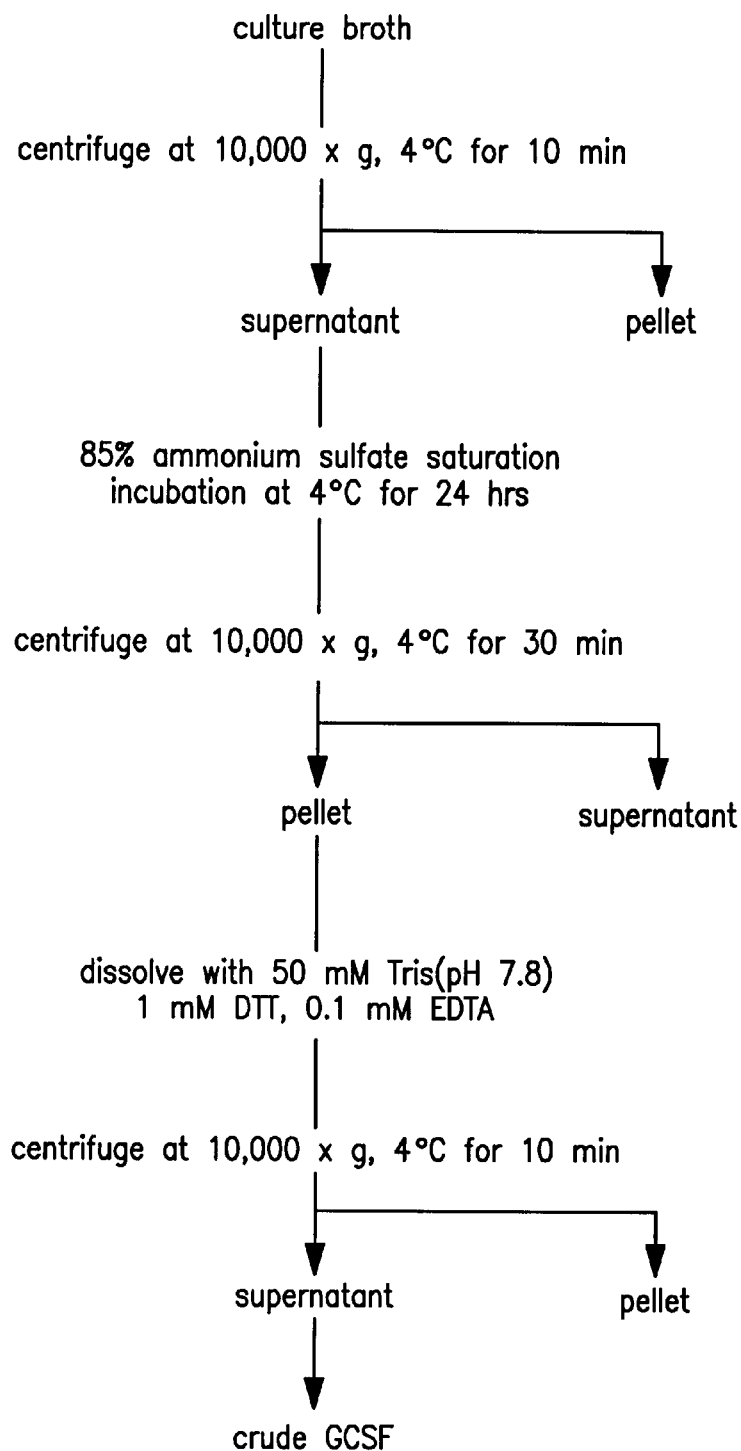
FIG. 13 shows a purification process of hGCSF in yeast culture broth

The present inventors pay attention to the fact that for the high-level production of recombinant hGCSF from yeast, the secretion efficiency should be enhanced as well as the expression level.

In order to secret a processed hGCSF, various secretory signals were fused to amino-terminal of hGCSF but the secretion was not successful.

Meanwhile it has been reported that interleukin 1β is efficiently secreted from yeast with a secretory signal [EMBO J. 6: 229–234 (1987)]. The present inventors paid attention to the possibility that amino acids of IL-1β amino terminal may be useful for secreting the processed hGCSF out of the yeast cell. The present inventors have finally found that hGCSF is successfully expressed and secreted out of cell when the fusion peptide consisting of a killer toxin secretory signal and 24 amino acids of IL-1β is placed in front of hGCSF gene. At this time, the dibasic KEX2 cleavage site was inserted between the N-terminal 24 residues of IL-1β and hGCSF and thereby, the mature hGCSF was released by proteolytic action of KEX2 enzyme (endopeptidase) in the secretory pathway.

The expression vector described above has arrangement of killer toxin secretory signal-24 amino acids of IL-1β-KEX2 cleavage site mature hGCSF. The protein expressed by using the above expressing vector is secreted through the following steps: the signal peptide is digested by signal peptidase during the translocation of the synthesized protein into Golgi, IL-1β region is excised by KEX2 peptidase, and then mature hGCSF with correct amino-terminal sequence is finally secreted.

The hGCSF expression vector used in the present invention will be described in detail as follows.

The hGCSF expression vector comprises: mating factor-α1 promoter replacing CYC-1 promoter in yeast expression vector YEpsec1-hI1 [C. Baldari et al., EMBO J. 6: 229–234 (1987)], hybrid secretory signal consisting of killer toxin leader sequence which is optimized by yeast codon usage and 24 amino-terminal of IL-1β, hGCSF gene, and GAL4 which is GAL gene activator. *Saccharomyces cerevisiae* is transformed by this expression vector and then selected transformant in uracil-defective minimal media is used as a hGCSF-producing strain. As a result of recombinant gene expression in high cell dinsity cultures of this selected transformant, the extracellular hGCSF was produced in large amount, and the culture conditions for the cell growth and the hGCSF production in fermenter were systematically optimized.

The present inventors also have developed an expression vector consisting of promoter and signal leader peptide of heat shock protein, with which the expression of recombinant hGCSF is regulated by temperature-shift. Differently from other inducible yeast promoters such as GAL promoter induced by galactose, Pho 5 promoter induced by phosphorus-starvation, ADHII promoter induced by glucose-starvation, the promoter of heat shock protein (HSP) regulates the transcription and hence protein synthesis only by temperature control (37~42° C.). And the HSP is secreted from the cells by leader sequence (PNAS, 89: 3671–3675). The present inventors have developed a method of preparing hGCSF by using expression vector constructed by HSP150 promoter and leader sequence of HSP.

In addition, the inventors inserted XbaI site between the amino acid sequence of IL-1β and the KEX2 cleavage site in the mating factor α promoter-based expression vector described above for the purpose of facilitating the insertion of other heterologous genes.

The above expression vector can be used for the production of other recombinant proteins. Particulary in this invention, the structural gene of hGH was inserted into the expression vector above by using XbaI-BamHI fragment as a cloning site and the hGH was successfully expressed from the selected transformant. Also, in the high cell ensity cultures of the selected transformant above, the hGH was successfully synthesized and secreted into the extracellular broth of fermenter in large quantity.

Ii is important to mention here that other recombinant proteins can be produced using the expression vector above although in this invention, the methods for producing hGCSF and hGH are only presented.

The amount of hGH production in the above high cell density fermentation is more than 1 g/L, which is relatively very high level compared to the fermentation yield of other yeast-derived recombinant proteins, reported in the past. Therefore, it may be possible that other recombinant proteins are expressed an efficiently secreted from yeast by employing the expression vector using the sequence comprising killer toxin leader sequence-amino terminal 24 residues of IL-1β-hGH as a hybrid signal peptide.

The present invention will be described in detail with examples. Examples are only for showing this invention, but does not limit the range of the claims of the present invention.

1. The Preparation of YEp2-k

Expression vector YEpsec1-hI1 consists of upstream activation sequence of GAL1, 10 gene, CYC-1 promoter, killer toxin leader sequence of Kluyveromyces lactics [M. J. R. Stark et al., NAR 12: 6011–6031 (1984)] and interleukin-1β gene, and IL-1β is expressed by the inducer, galactose.

To make the expression vector YEpsec1-hI1 more effective, killer toxin leader sequence was optimized, and CYC-1 promoter was substituted with more effective MFα1 promoter.

In order to terminate mRNA transcription, transcription terminator of GAPDH is added to the 3' terminus of hGCSF, and Gal 4 gene which is activator of Gal gene, is cloned and added into the expression vector.

1) Codon Optimization of Killer Toxin Leader Sequence the Formation of YEpsec-ok

EXAMPLE 1

Synthesis of Oligonucleotide of Killer Toxin Leader Sequence

In order to substitute codons of killer toxin leader sequence of the yeast expression vector YEpsec1-hI1 with the codons which encode proteins which are overexpressed in *Saccharomyces cerevisiae,* the oligonucleotide having sequences of SEQ ID NO:1 was synthesized by synthesizer (ABI, 392 DNA/RNA synthesizer) (J. Bennetzen, B. Hall J. Biol. Chem. 257: 3026–3031).

To insert the synthesized oligonucleotide into the site at which killer toxin leader sequence of YEpsec1-hI1 is cut out, the following reactions are followed. Each 5' terminus of oligonucleotide was phophorylated by T4 polynucleotide kinase(NEB) in the 30 μl of reaction solution [70 mM Tris-HCl(pH 7.6), 10 mM MgCl$_2$, 5 mM DTT(dithiotreitol)] containing ATP at 37° C. for 1 hr. Two reaction solutions were mixed and were left for 20 minutes. The oligonucleotides were annealed, while cooling to 30° C. slowly.

EXAMPLE 2

The Digestion of YEpsec1-hI1

1 μg of YEpsec1-hI1 was digested with restriction enzymes(SacI, KpnI; NEB) at 37° C. for 1 hr in the 40 μl reaction solution (20 mM Tris-acetate, 10 mM magnesium acetate, 50 mM potassium acetate), and then separated by electrophoresis in 1% slab agarose gel. After separation, 8.4 kb band was sliced and was eluted from the sliced DNA band by using Jetsorb(GENOMED, cat # 110300), and was purified.

EXAMPLE 3

The Ligation of DNA and Transformation

The oligonucleotides of killer toxin leader sequence annealed in the example 1 and YEpsec1-hI1 digested with restriction enzymes, SacI and KpnI in the example 2 were ligated by 100 unit of T$_4$ DNA ligase in 30 μl reaction solution, consisting of 50 mM Tris-HCl, 10 mM MgCl2, 10 mM DTT, and 1 mM ATP at 16° C. overnight. *E.coli* XL-1 Blue (supE44 hsdR17 recA1 end A1 gyrA46 thi relA1 Iac⁻F' [proAB⁺ lacI$^q$ lacZΔ M15 Th(tetr)]) was transformed with ligation reaction solution by CaCl2 method according to Molecular Cloning A Laboratory Manual (Sambrook, Fritch Mantiatis, 2nd adition, CSH). After transformation, transformed *E.coli* was spread on the LB-Amp agar plate media (10 g/1 trypton, 5 g/1 yeast extracts, 10 g/1 NaCl, 100 μg/ml ampicilin), and incubated for 20 hrs at 37° C. After the colony of ampicilin-resistant transformant(Amp$^R$) was cultured in the 1.5 ml of liquid LB-Amp media, the plasmid was eluted by alkali lysis method and purified by using RPM rotation filter (BIO 101). The plasmid which is not digested by restriction enzyme SmaI is selected and named as YEpsec-ok because the restriction enzyme SmaI site disappears on the killer toxin leader sequence by the step of the codon optimization.

EXAMPLE 4
Single Stranded DNA

To identify the base sequence of killer toxin leader sequence substituted for the purpose of codon optimization, the sequenscing of YEpsec-ok was conducted. The single stranded DNA necessary for sequencing is prepared as follows.

YEpsec-ok obtained in the example 3 was digested by restriction enzyme BamH1, SacI again, and electrophoresed at the 1.5% agarose gel, and 0.66 kb DNA fragment was sliced. After this DNA was eluted from agarose gel using GENE CLEAN KIT II. 1 μg of vector M13mp19 was digested by restriction enzyme BamHI, SacI, and then was purified by using GENE CLEAN KIT II. 0.66 kb DNA and M13mp19 was ligated by T$_4$ DNA ligase in the ligation mixture for 16° C. overnight. After competent E.coli XL-1 Blue was transformed with a reaction solution, single-stranded DNA was isolated according to the Molecular Cloning A Laboratory Manual(ibid). More specifically, 200 μl of XL-1 Blue solution cultured overnight, 40 μl of X-Gal (20 mg/ml in dimethylformamide) and 4 μl of IPTG (200 mg/ml) were mixed with agar, the mixture was spread on LB agar plate media. After the transformed E.coli was incubated at 37° C., one white plaque was picked on the agar plate. The picked plaque infected 200 μl XL-1 Blue with 20 ml LB at 37° C., and cultured for 5 hrs at 250 rpm. After this, the cultured solution was centrifuged, and 1/5 volume of PEG (20% PEG 8000 in 2.5M Nacl) was added to supernatant and left on ice for 15 minutes. After centrifugation the supernatant was discarded. Precipitated M13 virus pellet was suspended in 200 μl of TE buffer solution(10 mM Tris-HCl(pH 7.6), 1 mM EDTA) and then protein was extracted with phenol/chloroform/isoamylalcohol(25:24:1). After centrifugation, 2 volume of ethanol was added to supernatant to precipitate DNA, and DNA pellet was washed with 70% ethanol. After the pellet was dried by vacuum, the pellet was dissolved in 20 μl of distilled water.

EXAMPLE 5
Sequence Analysis

The base sequence of single-stranded plasmid prepared in the example 4 was analyzed by dideoxy chain termination DNA sequencing method. The primer used in sequencing was synthesized with ABI synthesizer.

Oligo DNA for analysis of base sequence has the sequences of SEQ ID No:2.

According to the result of analysis of base sequence, it is shown that the bases of the codons were substituted into the optimized codon as described in SEQ ID No:3.
2) The Preparation of Transcription Terminator of GAPDH (glyceraldehyde 3-phosphatase Dehydrogenase) (YEpsec-term)

EXAMPLE 6
Synthesis of Oligonucleotide

In order to terminate the transcription by GAL1, 10 UAS(upstream activation sequence)-MFα1 promoter, the transcription terminator of GAPDH with the sequences of SEQ ID NO:4 was synthesized [J. Biol. Chem. 245:839–845 (1979)].

After synthesis, the oligonucleotides were purified by OPC(oligo purification column), and were phosphorylated and annealed according to the example 1.

EXAMPLE 7
Digestion of YEpsec1-hI1

In order to insert the transcription terminator of GAPDH to the downstream of expressed gene, YEpsec1-hI1 was digested by restriction enzyme BamHI, SalI at 37° C. for 1 hr. The digested plasmid was electrophoresed in 1% slab agarose gel, and 9 kb band was sliced, and DNA was eluted from the cut band by using Jetsorb.

EXAMPLE 8
Ligation of DNA and Transformation

YEpsec1-hI1 digested by restriction enzyme BamH1, SalI and transcription terminator oligonucleotide of GAPDH which is phosphorylated and annealed in the example 6 were ligated by T$_4$ DNA ligase at 16° C.

Ampicilin-resistant colony obtained by transforming E. coli XL-1 Blue by reaction solution according to CaCl$_2$ method was cultured in the 1.5 ml LB-amp media. After culture, the plasmid was purified by RPM filter. Plasmid was digested by restriction enzyme BamHI, SalI, and was electrophoresed in 8% PAGE(Polyacrylamide gel electrophoresis). The plasmid with 70 bp DNA band was named as YEpsec-term.
3) Preparation of YEpsec-kt

EXAMPLE 9
Digestion of YEpsec-ok

1 μg of YEpsec-ok was digested by restriction enzyme KpnI, SalI at 37° C. for 1 hr, and was separated in 1% slab agarose gel. About 8.3 kb band was sliced and DNA was purified by Jetsorb.

EXAMPLE 10
Digestion of YEpsec-term

1 μg of YEpsec-term is digested by restriction enzyme KpnI, SalI at 37° C. for 1 hr. After this, plasmid was separated in 1% slab agarose gel and the 0.6 kb band was sliced and DNA was eluted.

EXAMPLE 11
Ligation of DNA and Transformation 0.6 kb of fragment eluted in the example 10 and 8.3 kb of vector eluted in the example 9 were dissolved in 30 μl of ligation solution, and was ligated by T$_4$ DNA ligase. The E. coli XL-1 Blue was transformed with reaction solution by CaCl$_2$ method. Ampicilin-resistant colony was cultured in the 1.5 ml of LB-Amp media, and plasmid was isolated by RPM rotation filter. The plasmid was digested by restriction enzyme, and the plasmid with transcription terminator to the YEpsec-ok was named as YEpsec-kt.
4) Substitution CYC-1 Promoter with MFα1 Promoter (The Preparation of YEp-αkt)

The original YEpsec1-hI1 consists of complex promoter of CYC-1 promoter and regulation region, GAL1, 10 UAS on which Gal4 protein, activator of genes related to galactose metabolism, binds, but in this invention the CYC-1 promoter was substituted with MFα1 promoter which has more effective transcription initiation [Kurjan et al., Cell. 30: 933–943 (1982)].

EXAMPLE 12
PCR(Polymerase Chain Reaction) of MFα1 Promoter

For the convenience of cloning, MFα1 promoter was obtained by PCR, using primers which has proper restriction enzyme site.

At the 5' terminus of each primer, there are restriction enzyme SalI and SacI site. Primers for amplification of transcription initiation sequence of MFα1 has the sequences of SEQ ID NO:5 and SEQ ID NO:6 respectively.

The template used in PCR was the p70αT vector containing MFα1 promoter. 2 units of Vent DNA polymerase was added to 50 pmol of each primer and 100 μl of reaction solution [1 mM KCl, 10 mM $(NH_4)_2SO_4$, 20 mM Tris-HCl (pH 8.8), 2 mM $MgSO_4$, 0.1% Triton X-100] including 200 μM DNTP, and then the reaction was cycled 35 times by using PCR ROBOT(Fine Co.), with the following temperature program:

Pretreatment 94° C., 300 seconds;
Annealing 53° C., 40 seconds;
Extension 72° C., 40 seconds;
Denaturation 94° C., 40 seconds;
Postreaction 53° C., 300 seconds Amplified MFα1 promoter was electrophoresed in 1.5% slab agarose gel, and 150 bp DNA band was identified and eluted from the gel. Eluted DNA was digested with restriction enzyme SalI and SacI.

EXAMPLE 13
Digestion of YEpsec-kt

1 μg of YEpsec-kt was digested with restriction enzyme, XhoI and SacI at 37° C. for 1 hr. Digested plasmid was separated in 1% slab agarose gel and about 8.8 kb DNA band was sliced and DNA was eluted using Jetsorb.

EXAMPLE 14
Ligation and Transformation

MF α1 promoter which was prepared by digesting with SalI and SacI in the example 12 and 8.3 kb of vector which was digested with XhoI and SacI in the example 13 was ligated by $T_4$ DNA ligase in 30 μl of ligation solution. *E.coli* XL-1 Blue was transformed by reaction solution, and ampicilin-resistant transformed colony was cultured in 1.5 ml LB-Amp media, and plasmid was purified. Because plasmid can not be cut by XhoI and SalI when the XhoI site and SalI site is ligated correctly, the plasmid which can not be cut by XhoI, SalI was selected and named as YEpαkt.

5) Gal4 Gene (The Preparation of YEpαktGAL4)

When galactose is carbon source, genes related to galactose metabolism (Gal7,10,1, Gal2, Mel1) is expressed by activator GAL4 protein in yeast [Johnstone et al., Proc. Natl. Acad. Sci. USA. 79: 6971–6975 (1982)]. Such induction begins at the transcriptional level of each gene, and GAL4 protein acts as transcription activator. Gal1 (kinase)-Gallo (epimerase). site of YEpsec1-hI1 contains UAS which is binding site of GAL4 [Cirton et al., J. Bacteriol. 158: 269–278 (1984)]. YEpsec1-hI1 is yeast 2μ circle high-copy number plasmid. Because GAL4 protein is encoded by chromosomal DNA, the concentration of GAL4 protein which can bind at GAL1-10 USA is low when induced by galactose. It is difficult to express GAL4 protein sufficiently. In order to maintain sufficient amount of GAL4 protein, GAL4 gene was inserted into YEpsec1-hI1.

EXAMPLE 15
PCR of GAL4 Gene

For PCR of GAL4 gene the primers having sequences of SEQ ID NO:7 and SEQ ID NO:8 respectively were synthesized.

The template was genome DNA of Saccharomyces cerevisiae 2805.

The PCR has the following composition: 50 pmol of each primer, 100 μl of reaction solution [10 mM KCl, 10 mM $(NH_4)_2SO_4$, 20 mM Tris-HCl(pH 8.8), 6 mM $MgSO_4$, 0.1% triton X-100] including 200 μM dNTP, and the used polymerase was 2 units of Vent DNA polymerase by using PCR ROBOT(Fine Co.). The reaction is cycled 35 times, with the following temperature programme:

Pretreatment 94° C., 300 seconds;
Annealing 53° C., 50 seconds;
Extension 72° C., 260 seconds;
Denaturation 94° C., 50 seconds;
Postreaction 53° C., 300 seconds Amplified GAL4 gene was electrophoresed in 1% slab agarose gel, and about 3.5 kb DNA band was identified, and DNA was eluted from gel and digested by restriction enzyme EcoRI.

EXAMPLE 16
Preparation of pUCGAL4

After pUC18 was digested by restriction enzyme, EcoRI at 37° C. for 1 hr, digested plasmid was dephosphorylated by CIP (calf intestinal phosphatase, NEB). The plasmid digested by EcoRI was purified by using Jetsorb. The GAL4 gene and pUC 18 digested by EcoRI was ligated by $T_4$ DNA ligase in 30 μl of ligation solution at 16° C. overnight. *E.coli* XL-1 Blue was transformed according to $CaCl_2$ method, and colony was cultured, and plasmid was purified by RPM rotation filter. When the plasmid was digested by EcoRI, the one with 3.5 kb DNA band was selected and named as pUCGAL4.

EXAMPLE 17
YEpαktGAL4

In order to insert GAL4 gene into YEpαkt, the following procedures were conducted.

pUCGAL4 was digested by restriction enzyme, EcoRI, and electrophoresed in 1% slab agarose gel, and about 3.5 kb DNA band was sliced, eluted from gel and purified. 1 μg of YEpαkt was digested by restriction enzyme, EcoRI at 37° C. for 1 hr, and the plasmid was dephosphorylated by CIP(calf intestinal phosphtase, NEB), and digested vector was purified by using Jetsorb. The GAL4 gene and YEpαkt digested by EcoRI was ligated by $T_4$ DNA ligase in the ligation solution at 16° C., overnight. *E.coli* XL-1 Blue was transformed according to $CaCl_2$ method, and colony was cultured and then plasmid was purified. When the plasmid was cut by EcoRI, 3.5 kb band was selected and named as YEpαktGAL4.

6) Preparation of YEp2-k

EXAMPLE 18
Preparation of YEp2-k

There are two digestion-site of restriction enzyme, KpnI on YEpαktGAL4. One is on the terminus of killer toxin leader sequence, and the other is on the selection marker, leu2-d gene. In this invention, since URA3 is used as selection marker of yeast, digestion-site of KpnI which is on leu2-d gene was destroyed. After YEpαktGAL was digested with KpnI partially, the digestion sites were filled by $T_4$ DNA polymerase in 50 μl of reaction solution [10 mM Tris-HCl pH 8.0, 5 mM $MgCl_2$, 5 mM DTT, 100 μM DNTP, 50 μg/ml BSA] at room temperature for 1 hr, and the KpnI site became blunt-ended. The site of blunt-ended KpnI was ligated by $T_4$ DNA ligase and ATP at 16° C. overnight. *E.coli* XL-1 Blue was transformed according to $CaCl_2$ method, and colony was cultured in 1.5 ml LB-Amp media, and then plasmid was purified. Plasmid was digested with restriction enzyme, and the plasmid which has not KpnI site on leu2-d gene was named as YEp2-k.

II. Cloning of GCSF (Preparation of YEp3KGC)

EXAMPLE 19

Preparation of hGCSF

For the PCR of GCSF, the oligonucleotides having the sequences of SEQ ID NO:9 and SEQ ID NO:10 respectively was synthesized.

Template used for PCR of hGCSF is macrophage cDNA library (Clontech). 2 units of Vent DNA polymerase was added to 50 pmol of each primer and 100 µl of reaction solution [10 mM KCl, 10 mM $(NH_4)_2SO_4$, 20 mM Tris-HCl (pH 8.8), 2 mM $MgSO_4$, 0.1% Triton X-100] including 200µ dNTP and then the reaction was cycled 35 times by using PCR ROBOT (Fine Co.) with the following temperature program:

Pretreatment 94° C., 300 seconds;

Annealing 53° C., 30 seconds;

Denaturation 94° C., 30 seconds;

Postreaction 53° C., 300 seconds

Amplified hGCSF gene was electrophoresed in 1% slab agarose gel, and 0.5 kb of DNA band was identified, purified and digested with KpnI and BamHI.

EXAMPLE 20

Digestion of YEp2-k After 1 µg of YEp2-k was digested with KpnI and BamHI, the digested DNA was electrophoresed in 1% slab agarose gel, and fragment of IL-1β was discarded and the rest of fragment of vector was eluted.

EXAMPLE 21

DNA Ligation and Transformation

GCSF gene and YEp2-k digested with KpnI and BamHI was ligated by $T_4$ DNA ligase in 30 µl of ligation solution. *E. coli* XL-1 Blue was transformed by reaction solution, and colony was cultured and then plasmid was purified. When the plasmid was digested with restriction enzyme, KpnI and BamHI, the plasmid which inserting fragment of GCSF was named as YEp2KGC.

III. Preparation of YEpGalMF

In order to express GCSF in general cloning vector, YEp352 [J. E. Hill et al., Yeast 2: 163–167 (1986)] the following procedure is conducted. The fragment necessary for the expression of GCSF was obtained from YpGX265Gal4, and the expression vector, YEpGalMF, was formed and used in the expression of GCSF.

EXAMPLE 22

PCR of GAL4-GAL1, 10 UAS-MFα1

UAS-MFα1 in the GAL4-GAL1, 10 was obtained from the YpGX265GAL4 [U.S. Pat. No. 5,013,652] by PCR, using the primer complementary to GAL4 and promoter of MFα1. Primers complementary to promoter of MFα1 and primer complementary to GAL4 have the sequence of SEQ ID NO:11 and SEQ ID NO:12 respectively.

2 units of Vent DNA polymerase was added to 500 pmol of each primer, 100 µl of reaction solution including 200 µl of dNTP, and then the reaction was cycled 35 times by using PCR ROBOT(Fine Co.) with the following temperature program:

Pretreatment 94° C., 300 seconds;

Annealing 53° C., 30 seconds;

Extension 72° C., 30 seconds;

Denaturation 94° C., 30 seconds;

Postreaction 53° C., 300 seconds

Amplified GAL4-GAL1, 10 UAS-MFα1 gene was electrophoresed in 1% slab agarose gel, about 4 kb of DNA band was identified, eluted from gel and digested with SacI and EcoRI.

EXAMPLE 23

Ligation of YEp352

1 µg of YEp352 was digested by SacI and EcoRI at 37° C. for 1 hr, and plasmid was electrophoresed in 1% slab agarose gel, and about kb DNA band was sliced and eluted by using Jetsorb.

Pretreatment 94° C., 300 seconds;

Annealing 50° C., 30 seconds

Extension 72° C., 30 seconds;

Denaturation 94° C., 30 seconds

Postreaction 53° C., 300 seconds

EXAMPLE 24

DNA Ligation and Transformation

The GAL4-GAL1, 10 UAS-MFα1 of YpGX256GAL4 and YEp352 digested with SacI, EcoRI was ligated by $T_4$ DNA ligase in the 30 µl of ligation solution. *E. coli* XL-1 Blue was transformed with reaction solution, and colony was cultured and then plasmid was purified. When the plasmid was digested with restriction enzyme, SacI, EcoRI, the 3.5 kb band was selected and named as YEpGalMF.

IV. Preparing of YEp2kIL20GC

EXAMPLE 25

Preparing of IL20GCSF

1) The primers having the sequences of SEQ ID NO:13 and SEQ ID NO:14 respectively were synthesized for PCR of killer toxin leader sequence, 24AA of amino terminus of IL-1β and cleavage site of endopeptidase KEX2.

YEp2-k was used as template. 2 units vent DNA polymerase was added to 50 pmol of each primer, 100 µl of PCR reaction solution including 200 µM of dNTP and then the reaction was cycled 35 times, with the following program:

Pretreatment 94° C., 300 seconds;

Annealing 50° C., 30 seconds;

Extension 72° C., 30 seconds;

Denaturation 94° C,, 30 seconds;

Postreaction 53° C., 300 seconds

Amplified killer toxin leader sequence, IL-β24 AA, was electrophoresed in 1.5% slab agarose gel, and about 80 bp DNA band was sliced, eluted from gel and purified. The DNA sequence amplified by PCR is SEQ ID NO:15.

2) GCSF is amplified by PCR by using the product of PCR described above 1) and oligonucleotide complementary to carboxyl terminus of GCSF.

The oligonucleotide complementary to carboxyl terminus of GCSF and having the sequences of SEQ ID NO:16 was synthesized.

YEp2KGC obtained from example 21 was used as template. 2 units Vent DNA polymerase was added to 50 pmol of each primer, DNA, of killer toxin sequence, 24AA of IL-1β and 100 µl of reaction solution including 20 µM of dNTP, and then the reaction was cycled 35 times, with the following temperature programme:

Pretreatment 94° C., 300 seconds;

Annealing 50 ° C., 30 seconds

Extension 72° C., 30 seconds:

Denaturation 94° C., 30 seconds;
Postreaction 53° C., 300 seconds
Amplified IL2OGCSF was electrophoresed in 1% slab agarose gel, and about 0.66 kb DNA band was sliced, eluted from gel and purified. IL20GCSF was digested with SacI, BamHI and purified.

EXAMPLE 26
EDigestion of YEp2-k
1 μg of YEp2-K was digested with SacI and BamHI at 37° C. for 1 hr. Digested plasmid was electrophoresed in 1% agarose gel, and about 12 kb DNA band was sliced and DNA was eluted by using Jetsorb.

EXAMPLE 27
DNA Ligation and Transformation
The IL20GCSF and YEp2-k digested with SacI and BamHI in the example 26 were ligated by $T_4$ DNA ligase in 30 μl of ligation solution. *E. coli* XL-1 Blue was transformed by the reacted solution, then colony was cultured, and the plasmids were purified. Plasmids were digested with restriction enzyme, and only the plsmids containing IL20GCSF was selected and named as YEp2kIL20GC.
V. Preparation of pIL2OGC

EXAMPLE 28
Digestion of YEp2kIL20GC
To obtain IL20GCSF-GAPDH transcription terminator from YEp2kIL20GC, the plasmid was digested with KpnI and SalI at 37° C. for 1 hr. The digested plasmid was separated by the same method as above, and DNA with the size of about 0.66 kb was purified.

EXAMPLE 29
Digestion of YEpGalMF
1 μg of YEpGalMF was digested by KpnI and SalI at 37° for 1 hr. The digested plasmid was separated and purified by the same method as above.

EXAMPLE 30
DNA Ligation and Transformation
IL20GCSF-GAPDH transcription terminator digested with KpnI and SalI and YEpGalMF were ligated by $T_4$ DNA ligase in 30 μl of ligation solution. And *E. coli* was transformed by the reacted solution. Colony was cultured and the plasmid was purified. The plasmid was digested by restriction enzyme, and the plasmid which was inserted by IL20GCSF-GAPDH transcription terminator was selected and named as pIL20GC.
VI. Preparation of YEpHSPGC
HSP 150 (heat shock protein) is a kind of glycoprotein which is secreted from yeast under cultivation at 37° C.–42° C. By using this property of HSP 150, the expression of hGCSF can be easily controlled. The HSP 150 promoter and secretion signal were cloned first, and then YEpHSPGC was prepared by inserting hGCSF gene.

EXAMPLE 31
PCR of HSP 150 Promoter and Leader Sequence
The primers having the sequences of SEQ ID NO:17 and SEQ ID NO:18 respectively were synthesized for PCR of HSP 150 promoter and leader sequence.
About 0.4 kb of HSP 150 promoter and leader sequence was amplified by PCR from *S. cerevisiae* genome DNA by using this primer. After purification, the plasmid was digested by KpnI and SalI.

EXAMPLE 32
Preparation of YEpHSPGC
MF(mating factor) α1 promoter and killer toxin leader sequence in YEp2kGC were substituted with HSP 150 promoter and leader sequence, and the plasmid was named as YEpHSPGC.
VII. Expression of hGCSF by using pIL20GC and YEp2kIL20GC

EXAMPLE 33
Transformation of Yeast
In order to express hGCSF in yeast, yeast was transformed by pIL20GC and YEp2kIL20GC.
*S. cerevisiae* 2805 (a, pep4:: HIS3, pro1-, can1, GAL1, his3 , ura3-52) was inoculated to 3 ml of YEPD media (1% of yeast extract, 2% of peptone, 2% of glucose), and cultured at 30° C. at 250 rpm overnight. The cultured cells were reinoculated into 15 ml of YEPD media. When OD600 is about 1.0 the culture was centrifuged and then competent yeast was prepared according to Alkali Cation-Yeast transform kit (Bio 101) protocol. Pellet of yeast was washed by TE buffer, suspended in lithium-acetate solution, and cultured at 30° C. at 120 rpm. After centrifuging the suspended solution, the pellet was suspended in TE buffer and mixed with transformable plasmid, vector DNA, and histamine in eppendorf tube. After the mixed solution was left at room temperature for 15 minutes, PEG was added to the mixed solution and the solution was left at 30° C. for 10 minutes. The reacted solution was treated by heat shock at 42° C. for 5 minutes, was centrifuged, and then was suspended in 200 μl of SOS media. The suspended solution was spread on SD agar plate media [0.8 g/l complete supplement Medium-URA (Bio 101), 6.7 g/l Yeast Nitrogen Base without Amino Acid (DIFCO), 2% glucose, 1.5% agar], was cultured at 30° C. for 3 days, and URA$^+$ colony was selected. Yeast transformed by pIL20GC was named as *Saccharomyces cerevisiae* GC1, yeast transformed by YEp2kIL20GC was named as *Saccharomyces cerevisiae* K2GC, and each strain was deposited to Korean Collection for Type Culture, KRIBB, Taejon, Korea in Sep. 27, 1995 (accession number: KCTC 0193BP and KCTC 0195BP, respectively).

EXAMPLE 34
Expression of GCSF
Colony was inoculated into SD media, and cultured at 30° C. at 250 rpm overnight. After the cultured solution was centrifuged the pellet was suspended in 1 ml of YEPGal media (1% Yeast extracts, 2% peptone, 2% galactose) and cultured at 30° C. at 250 rpm for 15 hrs in order to express hGCSF. The culture was centrifuged and 0.5 ml of the supernatant mixed with 10 μg/ml BSA and 10% TCA was left on ice for 20 minutes. Then it was centrifuged at 4° C. at 13,000 rpm for 10 minutes to precipitate hGCSF.
The pellet was dissolved in the solution containing 20 μl of distilled water and 20 μl of 2×SDS dye [125 mM Tris-HCl pH 6.8, 4% of SDS, 20% of glycerol, 10% of 2-mercaptoethanol], and the solution was electrophoretically analyzed using 16% SDS(dodecyl sodium sulfate)-PAGE gel [Laemmli, Nature. 227: 680–684], and the gel was stained with Coomasie blue. As a result, 18.7 kDa band of hGCSF was visualized.

EXAMPLE 35
Production of hGCSF in Fermentation Culture
a) Strain and Medium
The hGCSF was expressed and produced in fed-batch cultures of the yeast transformed by recombinant plasmid, pIL20GC. The seed media contains 20 g of glucose, 6.7 g of YNB (yeast nitrogen base) without amino acid, and 0.8 g of CSM-Ura (complete supplement mixture missing uracil) per liter. The composition of media used for batch and fed-batch cultivations is as follows.

| (1) Batch cultivation(per liter) | |
|---|---|
| a) KH$_2$PO$_4$ | 10 g |
| (NH$_4$)$_2$SO4 | 2 g |
| CaCl$_2$2H$_2$O | 0.5 g |
| NaCl | 0.5 g |
| trace metal solution | 10 ml |
| vitamin solution | 1 ml |
| Casamino acids | 5 g |
| Tween 80 | 0.6 g |
| b) MgSO$_4$ · 7H$_2$O | 0.5 g |
| c) glucose | 10 g |

Components a), b) and c) were autoclaved separately at 121° C. for 15 minutes.

| (2) Fed-batch cultivation | |
|---|---|
| 1) growth phase(per liter) | |
| a) (NH$_4$)$_2$SO$_4$ | 3 g |
| KH$_2$PO$_4$ | 5 g |
| vitamin solution | 3.5 ml |
| trace metal solution | 5 ml |
| Casamino acids | variable amounts |
| Tween 80 | 0.6 g |
| b) MgSO$_4$ · 7H$_2$O | 4 g |
| c) glucose | variable amounts |

The concentration ratio of sequence to casamino acids was ranged from 0.5 to 4.5 in the growth phase media.

| 2) Induction or product formation phase (per liter) | |
|---|---|
| a) (NH$_4$)$_2$SO$_4$ | 3 g |
| KH$_2$PO$_4$ | 5 g |
| vitamin solution | 3.5 ml |
| trace metal solution | 5 ml |
| Yeast extract | variable amounts |
| Tween 80 | 0.6 g |
| b) MgSO$_4$ · 7H$_2$O | 4 g |
| c) galactose | variable amounts |

The concentration ratio of glucose to yeast extract was ranged from 0.5 to 3 in the induction phase media.

Components a), b) and c) were autoclaved separately at 121° C. for 15 minutes.

Trace metal solution comprises per liter: 2.78 g of FeSO$_4$, 1.36 g of ZnCl$_2$.2H$_2$O, 0.8 g of CuSO4.5H$_2$O, 2.42 g of Na$_2$MoO$_4$.2H$_2$O, 2.38 g of CoCl$_2$.6H$_2$O and 1.69 g of MnSO$_4$.

Vitamin solution comprises per 100 mL: 0.6 g of inositol, 0.12 g of Ca-pantothenate, 0.12 g of pyridoxine HCl, 0.12 g of thiamine and 0.01 g of biotin.

b) Cultivation and hGCSF Production

After recombinant yeast was cultured on the agar plate media which has the same composition as the seed media, colony was suspended in 15% glycerol solution and stored at −70° C. At the time of cultivation, the recombinant yeast stored at −70° C. was spread on the above agar plate media and was cultured at 30° C., for 48 hrs. Then colony was inoculated into the seed media in shake flask (250 mL) and cultivated at 30° C. at 250 rpm. After 24 hrs, this seed culture was inocluted upto 5% of batch medium and cultivated in 5 L fermentor at 30° C., pH 5.5. When the glucose in the media is exhausted, the growth phase medium of fed-batch cultivation is added by pump connected to control module of fermentor. The medium feed rate was controlled with the following design equations to maintain glucose concentration below 100 mg/L.

$$\mu = \mu_0(S)\left(1 - \frac{X}{X_m}\right)$$

$$F_i = \frac{\mu X_i V_i}{S_0 Y_{x/s}}$$

$$V_{i+1} = V_i + F_i(\Delta t)$$

$$X_{i+1}V_{i+1} = X_i V_i \exp(\mu \Delta t)$$

$S_0$: glucose concentration in feed media (g/L)
X: yeast concentration in culture broth (g/L)
$X_m$: cell mass inhibition constant (g/L)
$\mu$: specific growth rate (hr-1)
V: culture volume (L)
F: volumetric feed rate (L/hr)
$\Delta t$: 30 sec When the concentration of yeast reached 25 to 35 g/L in the growth phase, the feed medium should be switched to induction phase medium. The volumetric feed rate was controlled to maintain the concentration of galactose at 10 to 35 g/L. The dissolved oxygen concentration was maintained above 40% of air saturation in fermentation broth by controlling the agitation speed and air flow rate. Culture samples were taken from fermenter for the analysis of cell density ethanol concentration, hGCSF concentration and plasmid stability. As a result, hGCSF was produced to the concentration of 230 mg/L in the fermentation broth, with suppressing ethanol accumulation and maintaining the plasmid stability above 90%.

VIII. Expression of hGCSF by Using YEpHSPGC

EXAMPLE 36

Transformation of Yeast and Expression of GCSF

*S. cerevisiae* 2805 was transformed by YEpHSPGC by using Alkali-Cation Yeast transform kit (Bio 101), and transformant was selected by Ura⁺. The yeast transformed by YEpHSPGC was named as *Saccharomyces cerevisiae* HGCA, and deposited to Korean Collection for Type Culture, KRIBB, Taejon, Korea in Sep. 27, 1995 (accession number: KCTC 0194BP). Colony of yeast which grew on SD media without uracil was inoculated into 3 ml of liquid media and incubated at 36° C. and at 250 rpm. Pellet precipitated after centrifugation was suspended in 1 mL YEP Gal media [1% yeast extract, 2% peptone, 2% galactose] and cultivated at 37° C. at 250 rpm, for 18 hr. After centrifuging the culture broth SDS dye was added to each of pellet and supernatant and protein was analyzed by 16% SDS-PAGE. In the supernatant, band of the induced recombinant protein was not visualized, but in the pellet fraction, a new major band appears at the size of 20.1 kDa. Western blotting was conducted by using hGCSF Ab (R&D system) and anti-mouse IgG-alkaline phosphatase and the protein at the size of 20 kDa was shown to be immunoreactive.

IX. Expression of hGCSF by Using pIL20XGC

EXAMPLE 37
Preparation of pIL20XGC

For the convenience of cloning, Xba I site was inserted into pIL2OGC.

1) PCR

At first, the oligonucleotide having the sequence of SEQ ID NO:19 which include XbaI site was synthesized by synthesizer (ABI, 392 DNA/RNA synthesizer).

The PCR was conducted by using the above primer and the primer of SEQ ID NO:20 complementary to mating factor α.

pIL20GC was used as template. 2 units Vent DNA polymerase was added to 100 µl of PCR reaction solution including 200 µM dNTP and 50 pmol of each primer, and then the reaction was cycled 35 times, with the following conditions:

Pretreatment 90° C., 60 seconds;
Annealing 45° C., 5 seconds;
Extension 72° C., 15 seconds;
Denaturation 94° C., 5 seconds;
Postreaction 53° C., 30 seconds Amplified DNA of killer toxin leader sequence-IL-1β-24-AA was separated by electrophoresis using 1.5% agarose gel, and DNA band of 80 bp size was eluted and purified. The DNA obtained by PCR has the base sequence of SEQ ID NO:21.

When XbaI site is inserted by preforming PCR, there is no change in the sequence of amino acid, but there is only substitution at the level of base sequence.

2) hGCSF gene was obtained from PCR by using PCR product synthesized above and the oligonucleotide complementary to the C-terminus of hGCSF gene.

The oligonucleotide complementary to C-terminus of hGCSF gene has the sequence of SEQ ID NO:22.

pIL20GC was used as template. 2 units Vent DNA polymerase was added to 100 µl of reaction solution including 50 pmol of primer, amplified DNA of killer toxin leader sequence-IL-1β-24AA-XbaI-KEX2, and 20 µM dNTP, and then the reaction was cycled 35 times, with the following conditions:

Pretreatment 95° C., 60 seconds;
Annealing 55° C., 5 seconds;
Extension 72° C., 15 seconds;
Denaturation 94° C., 7 seconds;
Postreaction 53° C., 30 seconds Amplified product (killer toxin leader-IL-1β N-terminal (24AA)-XbaI-KEX2-hGCSF) was separated by electrophoresis using 1% agarose gel, and DNA band size of 0.66 kb was eluted from gel, digested by restriction enzymes SacI and BamHI, and finally purified. 1 µg of pIL20GC was digested by SacI and BamHI at 37° C. for 1 hr. Digested plasmid was electrophoresed in 1% agarose gel, and DNA was eluted by using Jetsorb. The PCR product digested by SacI and BamHI and the plasmid pIL20GC were reacted in 30 µl of ligation reaction solution with the addition of T$_4$ DNA ligase. E. coli XL-1 Blue was transformed with the reaction mixture. And then plasmid was purified after cultivation of colony. The plasmid which was digested by restriction enzyme, XbaI was selected and named as pIL20XGC.

EXAMPLE 38
Transformation of Yeast

In order to express hGCSF in yeast, yeast was transformed by pIL20XGC. S. cerevisiae 2805 (a, pep4:: H153, pro 1δ, can1, GAL1, his 3δ, ura3-52) was inoculated into 3 mL of YEPD media and cultured at 30° C. at 250 rpm overnight. This was reinoculated into 15 mL of YEPD and centrifuged when OD$_{600}$ is about 1. Then competent yeast was prepared according to Alkali Cation -Yeast transform kit (Bio 101) protocol. Pellet of yeast was washed by TE buffer, suspended in the lithium acetate solution and shaked at 30° C. at 120 rpm. After centrifuging the suspension solution, the pellet was suspended in TE buffer and then was added to eppendorf tube including transformable plasmid, carrier DNA, and histamine. After kept at room temperature for 15 minutes, PEG solution was added to this solution and the resulting mixture was left at 30° C. for 10 minutes. After the mixture was heated at 42° C. for 5 minutes and centrifuged, the pellet was suspended in 200 µl of SOS media, spread on SD agar plate media and cultured at 30° C. for 3 days. Finally URA$^+$ colony was selected. This yeast strain was deposited to Korean Collection for Type Culture,KRIBB, Taejon, Korea in May 9, 1997 (accession number: KCTC 0330 BP).

EXAMPLE 39
Expression of hGCSF

The colony was inoculated into 3 mL of SD media and cultured at 30° C., 250 rpm, overnight. After centrifuging culture broth, the pellet was suspended in 1 ml of YEPGal medium and cultured at 30° C. at 250 rpm for 15 hrs, and finally hGCSF expression was induced. Same amount of 2×SDS dye [125 mM Tris-HCl, pH 6.8, 4% SDS, 20% glycerol, 10% 2-mercaptoethanol] was added to culture solution, and the solution was heated for 5 minutes. Proteins are separated in 15% of SDS PAGE [Laemmli; Nature. 227: 680–684] and stained by Coomassie blue. As a result, hGCSF was expressed at the same level in the case of using pIL20GC.

X. Purification of Expressed hGCSF Protein

EXAMPLE 40
Ammonium Sulfate Precipitation

After yeast cell culture was centrifuged for 10 minutes at 10,000×g, the supernatant was saturated at 85% with (NH$_4$)$_2$SO$_4$ and was left at 4° C. for 24 hrs. After centrifugation at 10,000×g for 30 minutes, the obtained pellet was dissolved in 50 mM Tris (pH 7.8) buffer solution including 0.1 mM EDTA and 1 mM DTT, and insoluble substance was removed by centrifugation at 10,000×g for 10 minutes. All experiments above were conducted at 4° C. hGCSF obtained from the above process was purified further by gel-permeation chromatography.

EXAMPLE 41
Gel-permeation Chromatography

Figure 14:
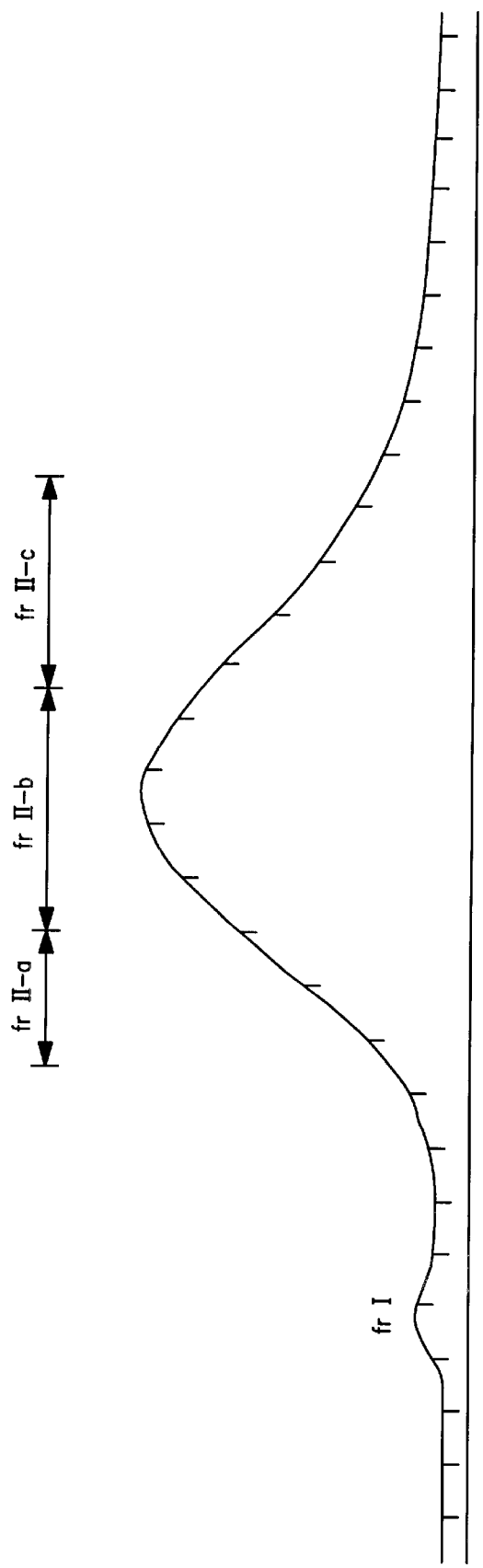
FIG. 14 shows a purification process of hGCSF via Sephacryl S-200 column chromatography

The media of gel-permeation chromatography, sephacryl-S-200 (Pharmacia) was washed by 50 mM Tris (pH 7.8) buffer solution including 1 mM DTT and 0.1 mM EDTA, and was packed into the column (1.6×0100 cm). The proteins in the 20 mL culture broth was concentrated by (NH$_4$)$_2$SO$_4$ precipitiation above and the concentrated solution was loaded on cloumn and eluted by 50 mM Tris (pH 7.8) buffer solution including 1 mM DTT and 0.1 mM EDTA. The proteins in each peak, obtained at the absorbance of 280 nm was concentrated by lyophilization. According to the results of SDS-PAGE analysis of each peak sample, hGCSF and some other proteins were contained in the first peak sample, and medium component peptides/proteins were contained in the second peak sample (FIG. 14). Most medium peptides/proteins was removed by sephacryl-S-200 gel filtration chromatography. Partially purified hGCSF sample by gel-permeation chromatography was subject to the next stage of C4 reversed-phase-HPLC.

Figure 15:
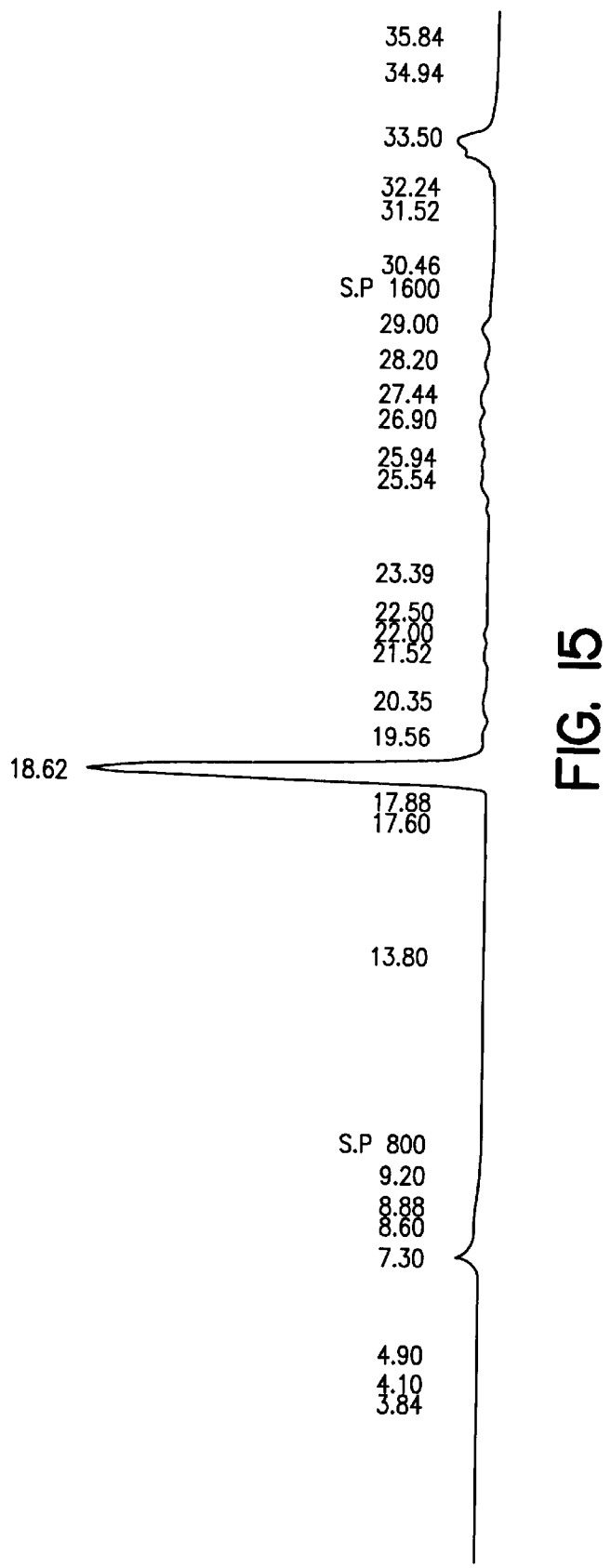
FIG. 15 shows the last step in the purification process of hGCSF

EXAMPLE 42
C4 Reversed-phase-HPLC hGCSF purified partially by gel-permeation chromatography was finally purified by using C4 column reversed-phase-HPLC. C4 column used was a product of Vydac company, and column size was 1.0×25 cm. Flow rate was 2 mL/min. After about 100 μg of material was injected. The column was runned with 0.1% TFA in water for 5 minutes and linear gradient in 0.1% TFA in acetonitrile was applied from 0 to 100%. The hGCSF was eluted at the gradient of 90% of 0.1% TFA in acetonitrile. By SDS-PAGE, it was confirmed that hGCSF was completely purified (FIG. 15). The recovery yield of hGCSF in the purification described in Example 44–46 above process was 8% and about 18 mg of purified hGCSF was obtained from 1 L culture broth.

XI. Analysis of N-terminal Amino Acid of Purified hGCSF

EXAMPLE 43
Analysis of N-terminal Amino Acid of Purified hGCSF hGCSF seperated by C4 reversed-phase-HPLC was blotted to PVDF membrane, and N-terminal amino acid sequence was determined.

The N-terminal amino acid sequence (SEQ ID NO: 26) corresponds to that of mature hGCSF (NH$_2$-Thr-Prb-Leu-Gly-Pro-COOH). This analysis was performed with technical assistance of Korean Basic Science Center. Protein sequencer used in analysis is Milligen 6600B, and PTH-amino acid derivative made by Edman degradation method was analyzed by HPLC.

mobile phase A: 35 mM ammonium acetate buffer (pH 4.8)
mobile phase B: 100% acetonitrile
temperature: 50° C.

| time (min) | flow rate (mL/min) | % A | % B | curve |
|---|---|---|---|---|
| INIT | 0.7 | 95 | 5 | * |
| 0.7 | 0.7 | 75 | 25 | 6 |
| 1.4 | 0.7 | 73 | 27 | 6 |
| 2.8 | 0.7 | 73 | 27 | 6 |
| 5.7 | 0.7 | 55 | 45 | 6 |
| 7.4 | 0.7 | 55 | 45 | 6 |
| 8.1 | 0.7 | 52 | 48 | 6 |
| 12.0 | 0.7 | 30 | 70 | 6 |
| 20.0 | 0.7 | 95 | 5 | 6 |

Amino acid sequence was also determined by using polymer coupling method. 5 mL of solution A was spotted on each side of membrane disk (PVDF) and the membrane disk was dried for 15–20 seconds. The membrane disk was put on heat board at 55° C., 30 mL of solution B was spotted thereon, and dried for 7 minutes (it was never dried over 10 minutes). 5 mL of solution C was spotted on each side of membrane disk, and dried for 15–20 seconds. And the membrane disk is put on 55° C. heat board, and 30 mL of solution D was spotted, and dried for 5 minutes. 20 mL of solution B was spotted and dried for 5 minutes, and membrane disk was washed with ethanol, water, and methanol.

A) PITC solution (10 nmol/μl of ethylacetate)
B) buffer solution (2% v/v triethylamine in 50% v/v in methanol)
C) DITC solution (0.1% w/v in ethylacetate)
D) polymer solution [0.10% w/v polyarylamine hydrochloride (low molecular weight) in B solution].

According to the result of analysis of amino acid by above method, threonine was analyzed at first cycle, prolin at the second cycle, leucine at the third cycle, glycin at the fourth cycle, and prolin at the fifth cycle. Therefore, the N-terminal amino acid sequence (SEQ ID NO: 27) of the hGCSF produced in this invention id NH$_2$-Thr-Pro-Leu-Gly-Pro, which corresponds to the N-terminus of authentic human hGCSF.

XII. Expression of hGH by Using pIL20XGH

EXAMPLE 44
PCR of Human Growth Hormone (hGH)

In order to conduct PCR of hGH, oligonucleotides complementary to N-terminus and C-terminus of mature human growth hormone and having the sequences of SEQ ID NO:23 and SEQ ID NO:24 respectively were synthesized.

2 units Vent DNA polymerase is added to 100 μl of reaction solution [10 mM of KCl, 10 mM of (NH$_4$)$_2$SO$_4$, 20 mM of Tris-HCl (pH 8.8), 2 mM of MgSO$_4$0.1% of Triton X-100] including 50 pmol of each primer and 200 μM of dNTP. Using human pituitary cDNA library as a template, PCR was cycled 35 times in conditions as follows.

Pretreatment 94° C., 60 seconds;
Annealing 60° C., 5 seconds;
Extension 72° C., 10 seconds;
Denaturation 94° C., 7 seconds;
Postreaction 531° C., 30 seconds DNA band at size of about 0.6 kb visualized on 1% agarose gel was purified and digested with restriction enzyme XbaI and BamHI. 1 μg of pIL20XGC was digested with restriction enzyme, XbaI and BamHI at 37° C. for 1 hr, and separated in 1% of agarose gel. Then fragment of hGCSF was removed and the rest part of vector was selected and eluted. The hGH gene and pIL20XGC digested with XbaI and BamHI were ligased by T$_4$ DNA ligase in 30 μl of ligation reaction solution. After E. coli XL-1 Blue was transformed by reaction mixtere, colony was cultured and then plasmid was purified. The plasmid was digested with restriction enzyme, XbaI and BamHI, and the plasmid which contains the hGH gene was selected and named as pIL2OXGH.

EXAMPLE 45
Transformation of Yeast

In order to express hGH in yeast, yeast was transformed by pIL20XGH. S. cerevisiae 2805 (a, pep4:: HIS3, pro1-δ, can1, GAL1, his3δ, ura3-52) was inoculated into 3 mL of YEPD media, and cultured at 30° C. at 250 rpm, overnight. Culture solution was reinoculated into 15 mL of YEPD and centrifuged at the time that OD$_{600}$ is about 1, and then competent yeast was prepared according to Alkali Cation-Yeast transform kit (BIO 101) protocol. Pellet of yeast was washed by TE buffer, suspended in lithium acetate solution, and shook at 30° C. at 120 rpm. The suspended solution was centrifuged, and the pellet was suspended in TE buffer and added to eppendorf tube including transformable plasmid, carrier DNA, and histamine. After the resultant was left at room temperature for 15 minutes, PEG was added to solution and left at 30° C. for 10 minutes. The above solution was treated by heat shock at 42° C. for 5 minutes, suspended in 200 μl of SOS media, spread on the SD agar plate media, and incubated at 30° C. for 3 days. Finally URA$^+$ colony was selected.

This strain of yeast was deposited to Korean Collection for Type Culture, KRIBB, Taejon, Korea in May 9, 1997 (accession number: KCTC 0331 BP).

EXAMPLE 46

Expression of hGH

Colony was inoculated in SD medium, and cultured at 30° C. at 250 rpm overnight. Culture solution was centrifuged, and the pellet was suspended in 1 mL of YEPGal media and cultured at 30° C. at 250 rpm for 15 hrs, to induce hGH expression. 2×SDS dye [125 mM Tris-HCl, pH 6.8, 4% SDS, 20% glycerol, 10% 2-mercaptoethanol] was added to culture solution, and the mixtere was heated for 5 minutes and electrophoresed by 15% SDS PAGE (Laemmli, Nature. 227: 680–684). The gel was stained by Coomasie blue, and hGH band corresponding to the size of about 22 kDa was detected.

EXAMPLE 47

Production of hGH in Fermentation Culture (a) Strain and Medium

The hGH was produced via fed-batch cultivation of the yeast transformed by recombinant plasmid pIL20XGH. The composition of seed media is the same as that used for the hGCSF fermentation. The composition of media used in batch and fed-batch cultivations is as follows.

(1) Batch Cultivation(per Liter)

Same as in Example 35.

| (2) fed-batch cultivation | |
|---|---|
| 1) growth phase(per liter) | |
| a) $(NH_4)_2SO_4$ | 3 g |
| $KH_2PO_4$ | 5 g |
| vitamin solution | 3.5 mL |
| trace metal solution | 5 mL |

| -continued | |
|---|---|
| (2) fed-batch cultivation | |
| Casamino acids | 136 g |
| Tween 80 | 0.6 g |
| b) $MgSO_4 \cdot 7H_2O$ | 4 g |
| c) glucose | 409 g |
| 2) induction phase or product formation phase (per liter) | |
| a) $(NH_4)_2SO_4$ | 3 g |
| $KH_2PO_4$ | 5 g |
| vitamin solution | 3.5 mL |
| trace metal solution | 5 mL |
| Yeast extract | 167 g |
| Tween 80 | 0.6 g |
| b) $MgSO_4 \cdot 7H_2O$ | 4 g |
| c) galactose | 333 g |

Components a), b) and c) were autoclaved separately at 121° C. for 15 min.

The composition of trace metal solution and vitamin solution is same as in Example 35.

(b) Cultivation and hGH Production

When the concentration of yeast reached 25 to 35 g/L in the growth phase, the feed media was switched to the induction phase media above. The feed rate of media was controlled in order to maintain the concentration of galactose in the culture broth at about 18 g/L. Unless otherwise mentioned, the culture storage and cultivation methods are the same as in Example 35. As a result, with negligible ethanol accumulation, and over 80% of plasmid stability hGH concentration in the culture broth was increased to 1300 mg/L.

We claim:

1. An expression vector comprising a hybrid secretion signal and a yeast-derived hybrid promoter, wherein said hybrid secretion signal comprises a DNA encoding 24 amino acids of the N-terminus of interleukin-1β and a yeast-derived killer toxin secretion signal and said yeast-derived hybrid promoter comprises a GAL1-10 upstream activation site (UAS) and a mating factor α-1 promoter.

2. The expression vector according to claim 1, further comprising a transcription terminator of glyceraldehyde 3'-phosphatase dehydrogenase (GAPDH) and a GAL4 gene.

3. The yeast expression vector Yep2-k, wherein said vector comprises a GAL UAS-Mfα-1 hybrid promoter, a killer toxin leader sequence, a GAPDH transcription terminator and a GAL4 gene.

4. The expression vector YEp2kIL20GC.

5. The expression vector pIL20GC.

6. The transformant, *Saccharomyces cerevisiae* K2GC (accession number: KCTC 0195 BP) transformed with the expression vector YEp2kIL20GC.

7. The transformant, *Saccharomyces cerevisiae* GC1 (accession number: KCTC 0193 BP) transformed with the expression vector pIL20GC.

8. An expression vector which comprises a hybrid promoter and a secretion signal of heat shock protein 150 (HSP 150), wherein said hybrid promoter comprises a GAL1-10 UAS and a promoter of HSP 150.

9. The expression vector YEpHSPGC.

10. The transformant, *Saccharomyces cerevisiae* HGCA (accession number: KCTC 0194 BP) transformed with the expression vector YEpHSPGC.

11. The expression vector pIL20XGC.

12. The transformant, *Saccharomyces cerevisiae* XGC (accession number: KCTC 0330 BP) transformed with the expression vector pIL20XGC.

13. A method for producing human granulocyte colony-stimulating factor (hGCSF) comprising the steps of:

(a) cultivating a transformant selected from the group consisting of the transformants of claim 6, claim 7, claim 10, and claim 12; and (b) recovering said hGCSF from the culture.

14. The expression vector pIL20XGH.

15. The transformant, *Saccharomyces cerevisiae* XGH (accession number: KCTC 0331 BP) transformed with the expression vector pIL20XGH.

16. A method for producing human growth hormone comprising the steps of:

(a) cultivating the transformant of claim 15; and (b) recovering said human growth hormone from the culture.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 1:

```
AGCTCTATAA AACAATGAAC ATCTTCTACA TCTTCTTGTT CTTGTTGTCT TTCGTTCGAG      60

GTAC                                                                  64
```

(2) INFORMATION FOR SEQ ID NO: 2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 2:

GTTTTCCCAG TCACTAC                                                           17

(2) INFORMATION FOR SEQ ID NO: 3:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 3:

GAGCTCTATA AAACAATGAA CATCTTCTAC ATCTTCTTGT TCTTGTTGTC TTTCGTTCAA            60

GGTACCCGGG GATCACTGAA C                                                      81

(2) INFORMATION FOR SEQ ID NO: 4:

(i) SEQUENCE CHARACTERISTICS:
        (A) LENGTH: 71 base pairs
        (B) TYPE: nucleic acid
        (C) STRANDEDNESS: double
        (D) TOPOLOGY: linear (ii) MOLECULE TYPE: oligonucleotide (xi) SEQUENCE DESCRIPTION: SEQ ID NO: 4:

GATCCCGGGT TTTTTATAGC TTTATGACTT AGTTTCAATT ATATACTATT TTAATGACAT            60

TTTCAGGTCG A                                                                 71

(2) INFORMATION FOR SEQ ID NO: 5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 5:

GTGCACTCGA GCCAAAAAGC AACAACAGGT TTTGG                                       35

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 6:

TTAATGAGCT CTATTGTGTA TGAAATTGAT AGTTTG                                      36

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 7:

AGTTTGAATT CCAACAGCAA GCAGGTGTGC AAGACA                                      36

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 8:

TCGAAGAATT CTCACCTTCG TGAACTTCAG AGGCGA                                      36

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 9:

AGGTAGGGTA CCACCCCCCT GGGCCCTGCC                                             30

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 10:

ATGGGAGGAT CCGGGCTTGG CTCAGGGCTG GGC                                         33

(2) INFORMATION FOR SEQ ID NO: 11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 11:

TTAATGAGCT CTATTGTGTA TGAAATTGAT AGTTTG                                      36

(2) INFORMATION FOR SEQ ID NO: 12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 12:

AGTTTGAATT CCAACAGCAA GCAGGTGTGC AAGACA                                      36

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: oligonucleotide (xi) SEQUENCE DESCRIPTION: SEQ ID NO: 13:

```
ACAATAGAGC TCTATAAAAC A                                              21
```

(2) INFORMATION FOR SEQ ID NO: 14:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 14:

```
GGCAGGGCCC AGGGGGGTTC TCTTGTCCAA AGAAACAGGT TTCAGTTCAT ATGG          54
```

(2) INFORMATION FOR SEQ ID NO: 15:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (ii) MOLECULE TYPE: oligonucleotide (xi) SEQUENCE DESCRIPTION: SEQ ID NO: 15:

```
ACAATAGAGC TCTATAAAAC AATGACCATC TTCTACATCT TCTTGTTCTT GTTGTCTTTC    60
GTTCAAGGTT TGTCACTGAA CTGCACGCTC CGGGACTCAC AGCCAAAAAG CTTGGTGATG   120
TCTGGTCCAT ATGGACTGAA AGCTGGTGTT TCTTTGGACA AGAGAACCCC CCTGGGCCCT   180
GCC                                                                183
```

(2) INFORMATION FOR SEQ ID NO: 16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 16:

```
ATGGGAGGAT CCGGGCTTGG CTCAGGGCTG GGC                                 33
```

(2) INFORMATION FOR SEQ ID NO: 17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 17:

CTAGCAGTCG ACGATAAGTC GCCAACTCAG CCT     33

(2) INFORMATION FOR SEQ ID NO: 18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 18:

CTAGCAGGCA CCGGCCAAAG TAGTAGCGGC CAA     33

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 19:

TCTCTTGTCT AGAGAAACAG CT     22

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 20:

ACAATAGAGC TCTATAAAAC A     21

(2) INFORMATION FOR SEQ ID NO: 21:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 21:

ACAATAGAGC TCTATAAAAC AATGAACATC TTCTACATCT TCTTGTTCTT GTTGTCTTTC     60

GTTCAAGGTT TGTCACTGAA CTGCACGCTC CGGGACTCAC AGCCAAAAAG CTTGGTGATG    120

TCTGGTCCAT ATGGACTGAA AGCTGGTGTT TCTCTAGACA AGAGA                    165

(2) INFORMATION FOR SEQ ID NO: 22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 22:

```
ATGGGAGGAT CCGGGCTTGG CTCAGGGCTG GGC                                   33
```

(2) INFORMATION FOR SEQ ID NO: 23:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 23:

```
TGTTTCTCTA GACAAGAGAT TCCCAACCAT TCCCTTATCC AGG                        43
```

(2) INFORMATION FOR SEQ ID NO: 24:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 24:

```
ATGCCAGGAT CCCAGCTAGA AGCCACAGCT GCCCTCCACA                            40
```

(2) INFORMATION FOR SEQ ID NO: 25:

(i) SEQUENCE CHARACTERISTICS:
        (A) LENGTH: 241 amino acids
        (B) TYPE: amino acid
        (D) TOPOLOGY: linear (ii) MOLECULE TYPE: PROTEIN (xi) SEQUENCE DESCRIPTION: SEQ ID NO: 25:

```
Met Asn Ile Phe Tyr Ile Phe Leu Phe Leu Leu Ser Phe Val Gln Gly
1               5                   10                  15

Thr Arg Gly Ser Leu Asn Cys Thr Leu Arg Asp Ser Gln Gln Lys Ser
            20                  25                  30

Leu Val Met Ser Gly Pro Tyr Glu Leu Lys Ala Gly Val Ser Leu Asp
        35                  40                  45

Lys Arg Phe Pro Thr Ile Pro Leu Ser Arg Leu Phe Asp Asn Ala Met
    50                  55                  60

Leu Arg Ala His Arg Leu His Gln Leu Ala Phe Asp Thr Tyr Gln Glu
65                  70                  75                  80

Phe Glu Glu Ala Tyr Ile Pro Lys Glu Gln Lys Tyr Ser Phe Leu Gln
                85                  90                  95

Asn Pro Gln Thr Ser Leu Cys Phe Ser Glu Ser Ile Pro Thr Pro Ser
            100                 105                 110

Asn Arg Glu Glu Thr Gln Gln Lys Ser Asn Leu Glu Leu Leu Arg Ile
        115                 120                 125

Ser Leu Leu Leu Ile Gln Ser Trp Leu Glu Pro Val Gln Phe Leu Arg
    130                 135                 140

Ser Val Phe Ala Asn Ser Leu Val Tyr Gly Ala Ser Asp Ser Asn Val
145                 150                 155                 160

Tyr Asp Leu Leu Lys Asp Leu Glu Glu Gly Ile Gln Thr Leu Met Gly
                165                 170                 175

Arg Leu Glu Asp Gly Ser Pro Arg Thr Gly Gln Ile Phe Lys Gln Thr
            180                 185                 190
```

```
                    -continued

Tyr Ser Lys Phe Asp Thr Asn Ser His Asn Asp Asp Ala Leu Leu Lys
        195                 200             205

Asn Tyr Gly Leu Leu Tyr Cys Phe Arg Lys Asp Met Asp Lys Val Glu
        210                 215             220

Thr Phe Leu Arg Ile Val Gln Cys Arg Ser Val Glu Gly Ser Cys Gly
225                 230                 235             240

Phe
```